United States Patent
Tan et al.

(10) Patent No.: US 9,879,238 B2
(45) Date of Patent: Jan. 30, 2018

(54) PHYTASE

(71) Applicant: BASF Enzymes LLC, San Diego, CA (US)

(72) Inventors: Xuqiu Tan, San Diego, CA (US); Arne I. Solbak, Jr., San Diego, CA (US)

(73) Assignee: BASF Enzymes LLC, San Diego, CA (US)

( * ) Notice: Subject to any disclaimer, the term of this patent is extended or adjusted under 35 U.S.C. 154(b) by 0 days.

(21) Appl. No.: 14/771,143

(22) PCT Filed: Mar. 10, 2014

(86) PCT No.: PCT/US2014/022432
§ 371 (c)(1),
(2) Date: Aug. 27, 2015

(87) PCT Pub. No.: WO2014/164442
PCT Pub. Date: Oct. 9, 2014

(65) Prior Publication Data
US 2016/0083700 A1    Mar. 24, 2016

Related U.S. Application Data

(60) Provisional application No. 61/777,139, filed on Mar. 12, 2013.

(30) Foreign Application Priority Data

May 16, 2013    (GB) .................................. 1308828.1

(51) Int. Cl.
*C12N 9/24*    (2006.01)
*C12N 9/16*    (2006.01)
(52) U.S. Cl.
CPC ........ *C12N 9/16* (2013.01); *C12Y 301/03008* (2013.01)
(58) Field of Classification Search
CPC ......... C12N 9/00; C12N 9/24; C12N 2800/10
See application file for complete search history.

(56) References Cited

U.S. PATENT DOCUMENTS

| | | | |
|---|---|---|---|
| 4,179,522 A | 12/1979 | Huitson | |
| 5,605,793 A | 2/1997 | Stemmer | |
| 5,707,843 A | 1/1998 | Monte | |
| 5,811,238 A | 9/1998 | Stemmer et al. | |
| 5,824,514 A | 10/1998 | Kauffman et al. | |
| 5,830,696 A | 11/1998 | Short | |
| 5,830,721 A | 11/1998 | Stemmer et al. | |
| 5,955,358 A | 9/1999 | Huse | |
| 5,965,408 A | 10/1999 | Short | |
| 6,171,820 B1 | 1/2001 | Short | |
| 6,238,884 B1 | 5/2001 | Short et al. | |
| 6,287,861 B1 | 9/2001 | Stemmer et al. | |
| 6,287,862 B1 | 9/2001 | Delcardayre et al. | |
| 6,291,242 B1 | 9/2001 | Stemmer et al. | |
| 6,309,872 B1 | 10/2001 | Rey et al. | |
| 6,335,179 B1 | 1/2002 | Short et al. | |
| 6,352,842 B1 | 3/2002 | Short et al. | |
| 6,358,709 B1 | 3/2002 | Short et al. | |
| 6,361,974 B1 | 3/2002 | Short et al. | |
| 6,440,668 B1 | 8/2002 | Short | |
| 6,537,776 B1 | 3/2003 | Short | |
| 6,764,835 B2 | 7/2004 | Short | |
| 8,334,124 B1 | 12/2012 | Mullaney et al. | |
| 8,361,956 B2 | 1/2013 | Malboobi et al. | |
| 8,877,478 B2 | 11/2014 | Steer et al. | |
| 2003/0054511 A1 | 3/2003 | Andela et al. | |
| 2005/0130160 A1 | 6/2005 | Chew et al. | |
| 2005/0186666 A1 | 8/2005 | Schneider et al. | |
| 2007/0196449 A1 | 8/2007 | Lei | |
| 2008/0058262 A1 | 3/2008 | Rasochova et al. | |
| 2009/0074909 A1 | 3/2009 | Webel et al. | |
| 2009/0263543 A1 | 10/2009 | Lohscheidt et al. | |
| 2012/0066781 A1 | 3/2012 | Weiner et al. | |
| 2016/0007633 A1 | 1/2016 | Han et al. | |
| 2016/0194618 A1 | 7/2016 | Solbak | |

FOREIGN PATENT DOCUMENTS

| | | |
|---|---|---|
| AU | 724521 B2 | 9/2000 |
| CN | 100406561 C | 7/2008 |
| CN | 101418276 A | 4/2009 |
| CN | 101883500 | 11/2010 |
| CN | 102586294 A | 7/2012 |
| CN | 102943083 A | 2/2013 |
| EP | 1659173 A1 | 5/2006 |
| WO | WO 93/16175 A1 | 8/1993 |

(Continued)

OTHER PUBLICATIONS

Watanabe, et al, (2009). Cloning and characterization of a novel phytase from wastewater treatment yeast *Hansenula fabianii* J640 and expression in Pichia pastoris. Journal of Bioscience and Bioengineering. 108(3), 225-230.

Wu, et al, (2004). Intracellular Expression of Bacillus Subtilis Phytase PhyC in Pichia Pastoris. Journal of Jishou University. 25(1), 36-41.

Xiong et al, (2006) High level expression of a synthetic gene encoding *Peniophora lycii* phytase in methylotrophic yeast *Pichia pastoris*. Applied Microbiology and Biotechnology, 72(5), 1039-1047.

(Continued)

*Primary Examiner* — Maryam Monshipouri
(74) *Attorney, Agent, or Firm* — Knobbe Martens Olson & Bear, LLP

(57) ABSTRACT

Polypeptides having phytase activity and polynucleotide sequences encoding the phytases are provided. The gene expresses the phytase at a level of at least 7 g/L to 40 g/L. The phytase have higher specific activity, retain activity at low pH, and retain activity at high temperature. The phytase can be used in a variety of compositions including food, feed, pharmaceuticals, and cleaning.

13 Claims, 7 Drawing Sheets

(56) References Cited

FOREIGN PATENT DOCUMENTS

| WO | WO 1999/008539 | 2/1999 |
|---|---|---|
| WO | WO 00/20569 A1 | 4/2000 |
| WO | WO 2000/071728 | 11/2000 |
| WO | WO 2001/029170 | 4/2001 |
| WO | WO 2001/090333 | 11/2001 |
| WO | WO 2002/095003 | 11/2002 |
| WO | WO 03/057247 A1 | 7/2003 |
| WO | WO 2005/007813 | 1/2005 |
| WO | WO 2005/056835 | 6/2005 |
| WO | WO 2005/074705 | 8/2005 |
| WO | WO 2006/028684 | 3/2006 |
| WO | WO 2007/142954 | 12/2007 |
| WO | WO 2008/036916 | 3/2008 |
| WO | WO 2009/018449 | 2/2009 |
| WO | WO 2009/073399 | 6/2009 |
| WO | WO 2010/135588 | 11/2010 |
| WO | WO 2011/0117396 | 9/2011 |
| WO | WO 2011/141613 | 11/2011 |
| WO | WO 2012/025462 | 3/2012 |
| WO | WO 2014/159185 | 10/2014 |
| WO | WO 2014/164442 | 10/2014 |

OTHER PUBLICATIONS

Extended European Search Report, dated Oct. 12, 2016, in European Patent Application No. EP14780237.5, dated Sep. 20, 2015.
Altschul, et al. (1997), "Gapped BLAST and PSI-BLAST: a new generation of protein database search programs", Nuc. Acids Res., 25(17):3389-3402.
Altschul et al. (1990), Basic Local Alignment Search Tool. J. Mol. Biol. 215(3):403-410.
Altschul et al. (1994), Issue in searching molecular sequence databases. Nature Genetics 6:119-129.
Blobel G, Walter P, Chang CN, Goldman B, Erickson AH, and Lingappa VR (1979) Translocation of proteins across membranes: The signal hypothesis and beyond. Symp. Soc. Exp. Biol. 33:9-36.
Bairoch, A. (2000), "The ENZYME database in 2000". Nucleic Acids Res. 28:304-305.
Demain, (2009) "Production of Recombinant Proteins by Microbes and higher Organisms," Biotechnology Advances, vol. 27, pp. 297-306.
Garcia et al. (1987), Wild type and mutant signal peptides of *Escherichia coli* outer membrane lipoprotein interact with equal efficiency with mammalian signal recognition particle J. Biol. Chem. 262, 9463-9468.
Gizzi (2008), "Determination of Phytase Activity in Feed: Interlaboratory Study", J. of AOAC International. vol. 91, No. 2, pp. 259-267.
Mata et al., (1997), "A hexameric phosphorothioate oligonucleotide telomerase inhibitor arrests growth of Burkitt's lymphoma cells in vitro and in vivo", Toxicol. Appl. Pharmacol. 144:189-197.
Ng DT, Brown JD, Walter P. (1996) Signal sequences specify the targeting route to the endoplasmic reticulum membrane. J Cell Biol. 134:269-278.
Pariza (2010), "Determining the safety of enzymes used in animal feed," Regulatory Toxicology and Pharmacology 56(3):332-342.
Pearson et al., (1988), "Improved tools for biological sequence comparison", Proc. Natl. Acad. Sci. USA 85(8):2444-2448.
Powers T. and Walter P. (1996) The nascent polypeptide-associated complex modulates interactions between the signal recognition particle and the ribosome. Curr. Biol., 6, 331-338.
Rice (1992), "Random PCR mutagenesis screening of secreted proteins by direct expression in mammalian cells", Proc. Natl. Acad. Sci. USA 89:5467-5471.
Samstag (1996), "Synthesis and properties of new antisense oligodeoxynucleotides containing benzylphosphonate linkages", Antisense Nucleic Acid Drug Dev 6(3):153-156.
Sapkota (2007), "What Do We Feed to Food-Production Animals? A Review of Animal Feed Ingredients and Their Potential Impacts on Human Health", Environ Health Perspect. May, 115(5): 663-670.
Selle et al. (2007), "Microbial phytase in poultry nutrition", Animal Feed Science and Technology, 135(1-2):1-41.
Sijmons et al., (1990), "Production of correctly processed human serum albumin in transgenic plants", Biotech. 8(3):217-221.
Strauss-Soukup et al. (1997), "Effects of neutralization pattern and stereochemistry on DNA bending by methylphosphonate substitutions", Biochemistry 36(29):8692-8698.
Thompson et al. (1994), "Clustal W: improving the sensitivity of progressive multiple sequence alignment through sequence weighting, position-specific gap penalties and weight matrix choice", Nucleic Acids Res. 22(22):4673-4680.
Von Heijne G. (1986), "A new method for predicting signal sequence cleavage sites", Nucleic Acids Res. Jun. 11, 1986; 14(11): 4683-4690.
International Preliminary Report on Patentability for International Patent Application No. PCT/US2014/022432 dated Sep. 24, 2015.
International Preliminary Report on Patentability for International Patent Application No. PCT/US2014/022433 dated Sep. 24, 2015.
International Preliminary Report on Patentability for International Patent Application No. PCT/US2014/022395 dated Feb. 4, 2016.
International Search Report and Written Opinion for International patent Application No. PCT/US2014/022432 dated Jul. 8, 2014.
International Search Report and Written Opinion for International Patent Application No. PCT/US2014/022395 dated Aug. 18, 2014.
International Search Report and Written Opinion for International patent Application No. PCT/US2014/022433 dated Jun. 16, 2014.
Supplementary Partial European Search Report dated Aug. 10, 2016, in European Application No. EP14774900, filed Oct. 6, 2015.
Gene Cloning, Expression and Characterization of Four Phytases from *Enterobacteriaceae*, Weina GU, Chinese Doctoral Dissertations Full-text Database Basic Sciences, No. 5, A006-27. Published Nov. 15, 2017.
First Office Action, dated Jun. 1, 2017, in Chinese Patent Application No. 201480014287.1, filed Sep. 11, 2015.
European Extended Search Report, dated May 26, 2017, in European Patent Application No. EP 14829460.6, filed Feb. 17, 2016.
Office Action, dated Feb. 10, 2017, in U.S. Appl. No. 14/409,840, filed Jan. 13, 2016.
Office Action, dated Mar. 9, 2017, in U.S. Appl. No. 14/770,766, filed Aug. 26, 2015.
Chinese First Office Action, dated Dec. 30, 2016, in corresponding Chinese Patent Application No. 201480013617, filed Sep. 10, 2015.
Chica et al., Curr Opin Biotechnol, Aug. 2005, 16(4):378-84.
Sen et al., Appl Biochem Biotechnol, Dec. 2007, 143(3):212-23.
Altschul et al., Basic Local Alignment, 1990; J Mol Biol. (1990) 215(3):403-410.
Ausubel et al., [Eds.] Current Protocols in Molecular Biology; John Wiley & Sons, Inc. (1998), TOC; 15 pages.
Bairoch, A.; The ENZYME database in 2000; nucleic Acids Res. (2000) 28;304-305.
Bickerstaff G.F. [Ed.] Immobilization of Enzymes and Cells: Some Practical Consideration; In Methods in Biotechnology, Humana Press, Totwa, NJ; (1997) Chapter 1, 16 pages.
Blobel et al., Translocation of proteins across membranes: The signal hypothesis and beyond. Symp Soc Exp Biol. (1979) 33:9-36; 18 pages.
Chica et al., Semi-rational approaches to engineering enzyme activity: combining the benefits of directed evolution and rational design. Curr Opin Biotech, (2005) 16:(4):378-384.
Crameri et al. , "Combinatorial multiple cassette mutagenesis creates all the permutations of mutant and wild-type sequences", Biotechniques, (1995); 18(2):194-196.
Demain et al., Production of recombinant proteins by microbes and higher organisms. Biotech Advances (2009) 27:297-306.
Higgins et al., "Using CLUSTAL for multiple sequence alignments", Methods Enzymol., (1996) 266:383-402.
Sijmons et al., Production of correctly processed human serum albumin in transgenic plants, Nature Biotech. (1990), 8(3):217-221.
Tijssen P., Hybridization with Nucleic Acid Probes: Part I: Theory and nucleic acid preparation; Elsevier Science Publishers BV (1993) Chapter 2; Overview; 62 pages.

PHYTASE

CROSS-REFERENCED TO RELATED APPLICATIONS

This application is a U.S. National Phase Application of PCT International Application Number PCT/US2014/022432, filed on Mar. 10, 2014, designating the United States of America and published in the English language, which is an International Application of and claims the benefit of priority to U.S. Provisional Application Ser. No. 61/777,139, filed on Mar. 12, 2013; and also claims the benefit of priority to Great Britain Patent Application Serial No. GB 1308828.1, filed on May 16, 2013. The disclosures of the above-referenced applications are herein expressly-incorporated by reference in their entireties.

SEQUENCE LISTING

This application is being filed electronically via the USPTO EFS-WEB server, as authorized and set forth in MPEP §502.05 and this electronic filing includes an electronically submitted sequence listing; the entire content of this sequence listing is hereby incorporated by reference into the specification of this application. The sequence listing is identified on the electronically filed ASCII (.txt) text file as follows:

| File Name | Date of Creation | Size |
|---|---|---|
| SEQUENCE_LISTING_VEREN067WO_D2500_1WO | Mar. 5, 2014 | 19.6 KB |

FIELD OF THE INVENTION

Polypeptides having phytase activity and polynucleotide sequences encoding the phytase are provided. In particular, the sequences provide increased levels of expression of a phytase having high specific activity, high thermostability, high thermotolerance, and various industrial uses of the phytase.

DESCRIPTION

Figure 1:
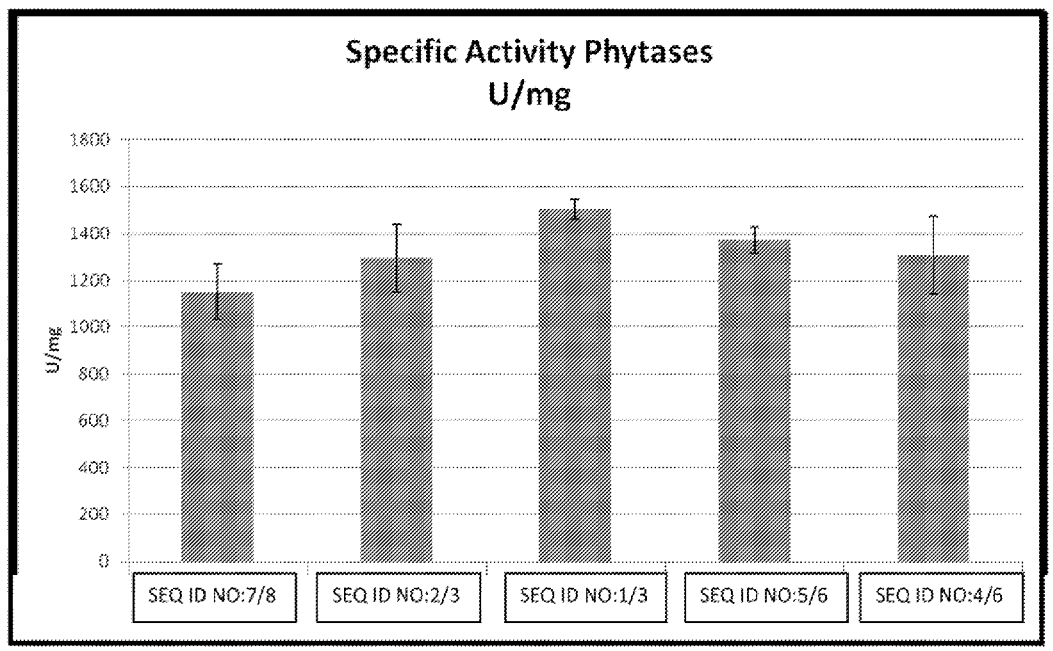
FIG. 1: Specific activity (U/mg) was determined on phytic acid (pH 5.5) with purified protein. *Pichia* expressed phytases: SEQ ID NO:8 (encoded by SEQ ID NO:7), SEQ ID NO:3 (encoded by SEQ ID NO:2), and SEQ ID NO:6 (encoded by SEQ ID NO:5) and *Pseudomonas* expressed phytases: SEQ ID NO:3 (encoded by SEQ ID NO:1) and SEQ ID NO:6 (encoded by SEQ ID NO:4).

Phytase is a phosphoric monoester hydrolase enzyme that catalyzes hydrolysis of phytic acid (myo-inositol-hexakis-phosphate) to phosphorus and inositol. According to the recommendations of the Nomenclature Committee of the International Union of Biochemistry and Molecular Biology (IUBMB) and Bairoch A., "The ENZYME database in 2000," Nucleic Acids Res 28:304-305(2000), a phytase is classified as Enzyme Commission (EC) number EC 3.1.3.8, and is also referred to as: 1-phytase; myo-inositol-hexakis-phosphate 3-phosphohydrolase; phytate 1-phosphatase; phytate 3-phosphatase; or phytate 6-phosphatase. Phytase is also classified as EC 3.1.3.26, which is also referred to as: 4-phytase; 6-phytase (name based on 1L-numbering system and not 1D-numbering); or phytate 6-phosphatase. Phytase is also classified as EC 3.1.3.72, which is also referred to as 5-phytase. Phytase is also referred to as histidine acid phosphatases (HAP); β-propeller phytases; purple acid phosphatase (PAP); and protein tyrosine phosphatases (PTPs). Alternative names for phytase will be known to those skilled in the art.

Phytase is an example of an enzyme that can have an effect as a supplement in animal feed pellets. Phytase degrades phytic acid into a myo-inositol core and one or more free phosphate molecules. Phytic acid consists of a myo-inositol core to which are covalently attached six phosphate groups. Phytic acid is a constituent of the plant material, such as soy bean seeds, that are used to generate feed pellets for animals such as non-ruminant animals, e.g. poultry, broilers, birds, chickens, layers, turkeys, ducks, geese, and fowl; ruminant animals e.g. cows, cattle, horses, and sheep; pigs, swine, piglets, growing pigs, and sows; companion animals including but not limited to: cats, dogs, rodents, and rabbits; fish including but not limited to salmon, trout, tilapia, catfish and carp; and crustaceans including but not limited to shrimp and prawn. Because these animals are unable to digest phytic acid, phytic acid has a number of detrimental effects. It chelates divalent cations such as Calcium and Magnesium, and its phosphate is in a form that is biologically unavailable to the animals being fed, resulting in a need to supplement the animal diet with these nutrients despite their being abundant in the feedstock. Furthermore, because these nutrients pass through the animal undigested, they are available to decomposers further down the food chain that are able to degrade phytic acid, resulting in, for example, algal blooms in surface waters to which the animal effluent comes into contact.

Non-ruminant animals such as chicken, pigs, and fish are unable to access sufficient phosphorus from food needed for rapid growth, as they do not naturally produce the phytase enzymes necessary to release the phosphorus from the phytic acid found in the food. Only a small amount of phosphorus is utilized from plant-based food and seeds, because the majority of phosphorus is present in the form of the phosphate groups of phytic acid (phytate). Therefore, a need exists to provide phosphorus to animals in order to increase their growth.

One solution is to add inorganic phosphorous supplements to the animal feed; however, the use of inorganic phosphorous supplements leads to an increased amount of phosphate excreted from the animal and into the environment, which leads to contamination of the water supply.

Another solution is to provide phytase supplements to the animal or to add phytase to animal feed. Examples of phytase products available commercially include but are not limited to: PHYZYME (Dupont, Danisco, Genencor); QUANTUM and FINASE (AB Vista, AB Enzymes); NATUPHOS (BASF); RONOZYME (DSM); Biofeed phytase (Novo Nordisk); Allzyme phytase (Alltech); OPTIPHOS (Enzyvia, Phytex, Cornell); Rovabio (Adisseo); PHYTOUT (US Waters). Each of these phytase products has limitations in at least production levels, production time, stability at high temperature, stability at low pH, specific activity, and dosage requirements. Therefore, a need exists for a phytase, for example, a phytase that can be produced with higher yields in less time, a phytase that retains more activity at high temperature, a phytase that retains more activity at low pH, or a phytase with higher specific activity that will enable users to reduce the dosage levels and reduce the cost for producing and providing a phytase for animal feed.

A phytase is a protein that is encoded by a nucleic acid sequence. The nucleic acid sequence or DNA is cloned into a host organism, which is able to express, or produce, the phytase. There are a variety of protein expression systems known in the art that can be used for production of proteins. Examples of protein expression systems include organisms such as: bacteria, yeasts, molds, mammals, plants, or insects. Various factors influence the selection of an expression system, such as the type of protein that is being expressed and the amount of the protein product produced. Demain, (2009) "Production of Recombinant Proteins by Microbes and higher Organisms," Biotechnology Advances, volume 27, pp 297-306, discloses various advantages and disadvantages of a variety of protein expression systems.

Phytase is commercially produced extracellulary from a variety of host organisms including but not limited to: *Aspergillus niger, Aspergillus oryzae, Penicillium funiculosum*, Phytase canola (*Brassica napus*), *Pichia pastoris*, and *Schizosaccharomyces pombe*, see Pariza, "Determining the safety of enzymes used in animal feed," Regulatory Toxicology and Pharmacology 56 (2010) 332-342.

Industrial scale production of a phytase requires an expression system that produces the high levels of enzyme in a short amount of time at a low cost. Therefore, a need exists to provide a gene that meets or exceeds the production requirements for industrial scale manufacturing of a phytase.

An embodiment of the invention is to provide a gene encoding a phytase which is produced at high levels in a gram-negative bacteria expression system. Another embodiment is to provide a gene encoding a phytase which is produced at high levels via intracellular expression. Another embodiment, is to produce a phytase in a gram-negative bacteria expression system, via intracellular expression, wherein the host organism is *Pseudomonas*. Another embodiment, is to produce a phytase in *Pseudomonas fluorescens*. The expression system could be any *Pseudomonas fluorescens* expression system known in the art, for example, the *Pseudomonas fluorescens* expression system that is commercially available from Dow Global Technologies Inc., strain DC454 (US Patent PUB. APP. NO. 20050130160 and US Patent PUB. APP. NO. 20050186666). A nucleic acid sequence encoding the phytase enzyme or polypeptide is inserted either in the pMYC vector (Dow Global Technologies Inc., US Patent PUB. APP. NO. 20050130160) or in the pDOW1169 vector (Dow Global Technologies Inc., US Patent PUB. APP. NO. 20080058262) and then introduced into the *Pseudomonas fluorescens* host by electroporation. Those skilled in the art will know alternative vectors that can be used as embodiments of this invention.

In another embodiment, the DNA encoding the phytase may be introduced, either on a plasmid or stably transformed into the genome of, for example, any number of gram negative bacterial systems such as *E. coli, Pseudomonas* species such as *fluorescens, Pseudomonas putida, Pseudomonas aeruginosa, Ralstonia* species, or *Caulobacter* species. Similarly, the phytase may be introduced into any number of gram positive bacterial expression systems such as *Bacillus* species such as *Bacillus subtilis, Bacillus megaterium*, or *Bacillus brevis Lactococcus* species such as *Lactococcus lactis, Lactobacillus* species, or *Streptomyces* species such as *Streptomyces lividans*. Other gram negative, gram positive or unrelated eubacterial or archaeal expression systems may be used to express the phytase.

In another embodiment, the DNA encoding the phytase may be introduced into a plasmid to direct its expression. Plasmids comprising the DNA encoding the phytase may include, for example, *E. coli* expression vectors of the families pQE, pET, and pASK; *Pseudomonas* expression vectors of the families pCN51 LT8, RSF1010, pWZ112T, and pMYC; *Bacillus* expression vectors of the families pBAX, pHT01, and pHIS1525; *Streptomyces* expression vectors of the families pIJ6021 and pIJ2460; and *Lactococcus*: expression vectors of the families pNZ9530 and pNZ8148, for example. These examples are for demonstrative purposes and do not represent a complete set of vectors in which the polynucleotide sequence of SEQ ID NO: 1 can be expressed.

In another embodiment, an isolated, recombinant, or synthetic nucleic acid sequence encoding a phytase is produced via intracellular expression at a level of at least 7.0 g/L, 8.0 g/L, 9.0 g/L, 10.0 g/L, 11.0 g/L, 12.0 g/L, 13.0 g/L, 14.0 g/L, 15.0 g/L, 16.0 g/L, 17.0 g/L, 18.0 g/L, 19.0 g/L, 20.0 g/L, 21.0 g/L, 22.0 g/L, 23.0 g/L, 24.0 g/L, 25.0, g/L, 26.0 g/L, 27.0 g/L, 28.0 g/L, 29.0 g/L, 30.0 g/L, 31.0 g/L, 32.0 g/L, 33.0 g/L, 34.0 g/L, 35.0 g/L, 36.0 g/L, 37.0 g/L, 38.0 g/L, 39.0 g/L, or at least 40.0 g/L or more than 40.0 g/L.

In another embodiment, the fermentation production time of the phytase is less than 150 hours, 145 hours, 140 hours, 135 hours, 130 hours, 125 hours, 120 hours, 115 hours, 110 hours, 105 hours, 100 hours, 95 hours, 90 hours, 85 hours, 80 hours, 75 hours, 70 hours, 65 hours, 60 hours, 55 hours, 50 hours, 49 hours, 48 hours, 47 hours, 46 hours, 45 hours, 44 hours, 43 hours, 42 hours, 41 hours, 40 hours, 39 hours, 38 hours, 37 hours, 36 hours, 35 hours, 34 hours, 33 hours, 32 hours, 31 hours, 30 hours, 29 hours, 28 hours, 27 hours, 26 hours, 25 hours, 24 hours, 23 hours, 22 hours, 21 hours, 20 hours or less than 20 hours.

In another embodiment, fermentation is performed at a volume of at or above 10 L, 100 L, 200 L, 500 L, 1000 L, 2000 L, 5000 L, 10,000 L, 25,000 L, 50,000 L, 55,000 L, 60,000 L, 65,000 L, 70,000 L, 75,000 L, 80,000 L, 85,000 L, 90,000 L, 95,000 L, 100,000 L, 110,000 L, 120,000 L, 130,000 L, 140,000 L, 150,000 L, 160,000 L, 170,000 L, 180,000 L, 190,000 L, 200,000 g/L or more than 200,000 L.

In one embodiment, the intracellular expression system is a gram-negative bacteria. In another embodiment, the gram-negative bacteria is a *Pseudomonas*. In another embodiment, the *Pseudomonas* is a *Pseudomonas fluorescens*.

In one embodiment, the polypeptide having phytase activity is produced at about 35.0 g/L. In another embodiment the polypeptide having phytase activity is produced at more than 7.0 g/L. In another embodiment the phytase will be expressed in less than 144 hours. In another embodiment, the phytase will be produced in less than 84 hours, 74 hours, 64 hours, 54 hours, 44 hours, 34 hours, or 24 hours.

In one embodiment, the nucleic acid encoding the phytase produced by intracellular expression is derived from or is a modified version of a nucleic acid derived from *E. coli*, a *Bacillus* sp., a *Hafnia* sp., *Perni ophora lycii*, a *Buttiauxella* sp., a *Citrobacter* sp., or *Aspergillus niger*. In another embodiment, the phytase is any phytase disclosed in PCT Publication No. WO 1999/008539, WO 2000/071728, WO 2001/090333, WO 2002/095003, WO 2006/028684, WO 2008/036916, or WO 2010/135588.

In another embodiment, the nucleic acid is an isolated, synthetic, or recombinant nucleic acid. In another embodiment, the isolated, recombinant, or synthetic nucleic acid sequence encodes a polypeptide having phytase activity. In another embodiment the nucleic acid sequence is selected from the group consisting of: a nucleic acid sequence of SEQ ID NO:1; SEQ ID NO:2, SEQ ID NO:4, SEQ ID NO:5, and SEQ ID NO:7

In one embodiment, the nucleic acid encoding a polypeptide having phytase activity is a variant of SEQ ID NO:1, SEQ ID NO:2, SEQ ID NO:4, SEQ ID NO:5, or SEQ ID NO:7 wherein the variant is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9%, or completely (100%) identical to SEQ ID NO:1, SEQ ID NO:2, SEQ ID NO:4, SEQ ID NO:5, and/or SEQ ID NO:7, or a fragment thereof, wherein the variant encodes a polypeptide having phytase activity.

In another embodiment, the isolated, synthetic, or recombinant nucleic acid sequence encodes a polypeptide selected from a group consisting of: SEQ ID NO:3, SEQ ID NO:6, and SEQ ID NO:8. In another embodiment, the nucleic acid of SEQ ID NO:1, or a variant of SEQ ID NO:1 encodes a polypeptide of SEQ ID NO:3. In another embodiment, the nucleic acid of SEQ ID NO:2, or a variant of SEQ ID NO:2 encodes a polypeptide of SEQ ID NO:3. In another embodiment, the nucleic acid of SEQ ID NO:4, or a variant of SEQ ID NO:4 encodes a polypeptide of SEQ ID NO:6. In another embodiment, the nucleic acid of SEQ ID NO:5, or a variant of SEQ ID NO:5 encodes a polypeptide of SEQ ID NO:6. In another embodiment, the nucleic acid of SEQ ID NO:7, or a variant of SEQ ID NO:7 encodes a polypeptide of SEQ ID NO:8.

In one embodiment, a nucleic sequence is complementary to the full length sequence of SEQ ID NO:1, SEQ ID NO:2, SEQ ID NO:4, SEQ ID NO:5, SEQ ID NO:7, or a variant thereof.

In one embodiment, the phytase is an isolated, recombinant, or synthetic polypeptide having phytase activity, wherein the polypeptide is selected from the group consisting of: an amino acid sequence of SEQ ID NO:3, SEQ ID NO:6, and SEQ ID NO:8.

In another embodiment, the phytase is a variant of SEQ ID NO:3, SEQ ID NO:6, or SEQ ID NO:8, wherein the variant is at least 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9%, or completely (100%) identical to SEQ ID NO:3, SEQ ID NO:6, or SEQ ID NO:8, or an enzymatically active fragment thereof, wherein the variant has phytase activity. In another embodiment, the phytase is an amino acid sequence encoded by the nucleic acid sequence comprising SEQ ID NO:1, SEQ ID NO:2, SEQ ID NO:4, SEQ ID NO:5, and/or SEQ ID NO:7.

In one embodiment, the phytase is an amino acid sequence lacking a signal sequence, a proprotein sequence, a promoter sequence, or any combination thereof.

In one embodiment, the phytase is an amino acid sequence further comprising a heterologous sequence selected from the group consisting of: a signal sequence, a tag, an epitope, a mating factor, a regulatory sequence, a promoter sequence, an N-terminal extension, a C-terminal extension, and any combination thereof.

In one embodiment, the phytase has a specific activity at any value in a range from about 1000 U/mg to about 1,600 U/mg. In another embodiment the phytase has a specific activity of 1000 U/mg, 1100 U/mg, 1200 U/mg, 1300 U/mg, 1400 U/mg, 1500 U/mg, or 1600 U/mg.

In one embodiment, the phytase is active at any pH ranging from about pH 1.0 to about pH 9.0. In one embodiment, the phytase is active at a pH of: 1.0, 1.5, 2.0, 2.5, 3.0, 3.5, 4.0, 4.5, 5.0, 5.5, 6.0, 6.5, 7.0, 7.5, 8.0, 8.5, 9.0, 9.5, or more alkaline conditions.

In one embodiment, the phytase is active at any temperature in a range from about 50 degrees C. to about 100 degrees C. In another embodiment, the phytase is active at a temperature in the range from greater than 37° C. to about 95° C., or between about 55° C. to about 85° C., or between about 70° C. to about 75° C., or between about 70° C. to about 95° C., between about 90° C. to about 95° C., between about 95° C. to about 105° C., or between about 95° C. to about 110° C.

In one embodiment, a phytase of the invention is included in a composition. In another embodiment, the composition is a formulation. In another embodiment, the composition is a food, a feed, a supplement, an animal feed additive, or a dietary aid comprising the phytase. In another embodiment, the composition is a pharmaceutical comprising the phytase.

"Cloning," as used herein is a process for creating copies of DNA fragments, cells, or organisms, wherein the DNA is introduced into a host organism that produces copies of the recombinant DNA.

"Cloning vector," as used herein is a carrier, such as a bacterial plasmid or bacteriophage, used to insert a genetic sequence, such as deoxyribonucleic acid (DNA) fragment or a complete gene, into a host cell such that the foreign genetic material is capable of being replicated.

"Cocktail" as used herein is a composition comprising the phytase of this invention in combination with one or more additional enzymes. The one or more additional enzymes can be any enzyme, for example, a lactase, a lipase, a protease, a catalase, a xylanase, a cellulase, a glucanase, a mannanase, an amylase, an amidase, an epoxide hydrolase, an esterase, a phospholipase, a transaminase, an amine oxidase, a cellobiohydrolase, an ammonia lyase, or any combination thereof.

A "codon" is a three polynucleotide sequence that specifies the identity of an amino acid to be added to a protein.

"Complementary DNA or cDNA," as used herein is DNA synthesized from a messenger RNA (mRNA) template in a reaction catalyzed by the enzyme reverse transcriptase and the enzyme DNA polymerase.

"Culturing," as used herein includes use of a conventional nutrient media modified as appropriate for activating promoters, selecting transformants or amplifying genes in host cells containing the polynucleotides that encode a phytase. The culture conditions, such as temperature, pH and the like, are those used with the host cell selected for expression, and will be apparent to the ordinarily skilled artisan.

"Host cell," as used herein is a transformed cell comprising a nucleic acid sequence encoding a phytase, or comprising an expression cassette, vector, cloning vehicle, expression vector, or cloning vector of the invention. The host cell may be any of the host cells familiar to those skilled in the art, including prokaryotic cells or eukaryotic cells, such as bacterial cells, fungal cells, yeast cells, mammalian cells, insect cells, or plant cells. The selection of an appropriate host is within the abilities of those skilled in the art.

Host cells can be used in a conventional manner to produce the gene product encoded by the recombinant sequence. Depending upon the host employed in a recombinant production procedure, the polypeptides produced by the host cells may be glycosylated or may be non-glycosylated. Polypeptides of the invention may or may not also include an initial methionine amino acid residue.

"Identical," as used herein is the extent of sequence identity (homology), which may be determined using any computer program and associated parameters known in the art, such as BLAST 2.2.2 or FASTA version 3.0t78, with the default parameters. Protein and/or nucleic acid sequence identities (homologies) may be evaluated using any of the variety of sequence comparison algorithms and programs known in the art. Such algorithms and programs include, but are not limited to a BLAST program (Basic Local Alignment Search Tool at the National Center for Biological Information, such as BLAST, BLAST2, BLASTN and BLASTX), TBLASTN, BLASTP, FASTA, TFASTA, and CLUSTALW (Pearson and Lipman, Proc. Natl. Acad. Sci. USA 85(8): 2444-2448, 1988; Altschul et al., J. Mol. Biol. 215(3):403-410, 1990; Thompson et al., Nucleic Acids Res. 22(2):4673-4680, 1994; Higgins et al., Methods Enzymol. 266:383-402, 1996; Altschul et al., J. Mol. Biol. 215(3):403-410, 1990; Altschul et al., Nature Genetics 3:266-272, 1993. BLAST, BLAST 2.0 and BLAST 2.2.2 algorithms are also used to practice the invention. They are described, e.g., in Altschul (1977) Nuc. Acids Res. 25:3389-3402; Altschul (1990) J. Mol. Biol. 215:403-410. Software for performing BLAST analyses is publicly available through the National Center for Biotechnology Information.

The terms "homology" and "identity" in the context of two or more nucleic acids or polypeptide sequences, refer to two or more sequences or subsequences that are the same or have a specified percentage of amino acid residues or nucleotides that are the same when compared and aligned for maximum correspondence over a comparison window or designated region as measured using any number of sequence comparison algorithms or by manual alignment and visual inspection. For sequence comparison, one sequence can act as a reference sequence (an exemplary sequence of the invention) to which test sequences are compared. When using a sequence comparison algorithm, test and reference sequences are entered into a computer, subsequence coordinates are designated, if necessary, and sequence algorithm program parameters are designated. Default program parameters can be used, or alternative parameters can be designated. The sequence comparison algorithm then calculates the percent sequence identities for the test sequences relative to the reference sequence, based on the program parameters.

"Nucleic acid," as used herein refers to an oligonucleotide, nucleotide, polynucleotide, or to a nucleic acid fragment of any of these. The nucleic acid can be genomic DNA, cDNA, synthetic DNA or RNA (e.g., mRNA, rRNA, tRNA) of genomic or synthetic origin which may be single-stranded or double-stranded and may represent a sense or antisense strand, to peptide nucleic acid (PNA), or to any DNA-like or RNA-like material, natural or synthetic in origin, including, e.g., iRNA, ribonucleoproteins (e.g., iRNPs). The term encompasses nucleic acids, i.e., oligonucleotides, containing known analogues of natural nucleotides. The term also encompasses nucleic-acid-like structures with synthetic backbones, see e.g., Mata (1997) Toxicol. Appl. Pharmacol. 144:189-197; Strauss-Soukup (1997) Biochemistry 36:8692-8698; Samstag (1996) Antisense Nucleic Acid Drug Dev 6:153-156.

The nucleic acids used to practice this invention, whether RNA, iRNA, antisense nucleic acid, cDNA, genomic DNA, vectors, viruses or hybrids thereof, may be isolated from a variety of sources, genetically engineered, amplified, and/or expressed/generated recombinantly. Recombinant polypeptides generated from these nucleic acids can be individually isolated or cloned and tested for a desired activity. In one embodiment, the nucleic acids can be in a recombinant expression system, including bacterial, mammalian, yeast, insect, or plant cell expression systems.

Techniques for the manipulation of nucleic acids, such as, e.g., subcloning, labeling probes (e.g., random-primer labeling using Klenow polymerase, nick translation, amplification), sequencing, hybridization and the like are well described in the scientific and patent literature, see, e.g., Sambrook, ed., MOLECULAR CLONING: A LABORATORY MANUAL (2ND ED.), Vols. 1-3, Cold Spring Harbor Laboratory, (1989); CURRENT PROTOCOLS IN MOLECULAR BIOLOGY, Ausubel, ed. John Wiley & Sons, Inc., New York (1997); LABORATORY TECHNIQUES IN BIOCHEMISTRY AND MOLECULAR BIOLOGY: HYBRIDIZATION WITH NUCLEIC ACID PROBES, Part I. Theory and Nucleic Acid Preparation, Tijssen, ed. Elsevier, N.Y. (1993).

The invention provides nucleic acid (e.g., DNA) sequences of the invention operatively linked to expression (e.g., transcriptional or translational) control sequence(s), e.g., promoters or enhancers, to direct or modulate RNA synthesis/expression. The expression control sequence can be in an expression vector.

The invention provides expression systems, e.g., expression cassettes, vectors, cloning vehicles and the like, comprising nucleic acids of the invention, e.g., sequences encoding the phytases of the invention, for expression, and overexpression, of the polypeptides of the invention.

Optimized expression of nucleic acid sequences of the invention also refers to directed or random mutagenesis of a nucleic acid to effect increased expression of the encoded protein. The mutagenesis of the nucleic acids of the invention can directly or indirectly provide for an increased yield of expressed protein. By way of non-limiting example, mutagenesis techniques described herein may be utilized to effect mutation of the 5' untranslated region, 3' untranslated region, or coding region of a nucleic acid, the mutation of which can result in increased stability at the RNA or protein level, thereby resulting in an increased yield of protein.

In some embodiments, the mutations to be made in a protein of interest are determined by various factors including analysis of the two dimensional and three dimensional structure of the 5 prime end of the predicted mRNA structure of an open reading frame (ORF) or gene of interest, as well as the preferred codons of the host, to select mutations which may enhance the expression of the protein of interest. For example, in some embodiments, the mutations are not selected solely on the basis of the preferred codons of the host, that is, codon optimization, nor a codon optimization program.

A "mutation" is a change in a nucleotide sequence or an amino acid compared to a reference.

A "silent mutation" is a mutation in a codon that does not result in the specification of a different amino acid.

A "nucleotide" refers to one of the four bases which comprise DNA sequence—Adenine (A), Thymidine (T), Guanidine (G), and Cytosine (C).

In one aspect, the expression cassettes of the invention comprise a sequence of the invention and a nucleotide sequence which is capable of affecting expression of a structural gene (i.e., a protein coding sequence, such as a phytase of the invention) in a host compatible with such sequences. Expression cassettes include at least a promoter operably linked with the polypeptide coding sequence; and, optionally, with other sequences, e.g., transcription termination signals. Additional factors necessary or helpful in effecting expression may also be used, e.g., enhancers.

Large numbers of suitable vectors are known to those of skill in the art, and are commercially available. Exemplary vectors include: bacterial: pQE vectors (Qiagen), pBluescript plasmids, pNH vectors, (lambda-ZAP vectors (Stratagene); ptrc99a, pKK223-3, pDR540, pRIT2T (Pharmacia); Eukaryotic: pXT1, pSG5 (Stratagene), pSVK3, pBPV, pMSG, pSVLSV40 (Pharmacia). However, any other plasmid or other vector may be used so long as they are replicable and viable in the host. Where a recombinant microorganism or cell culture is described as hosting an "expression vector" this includes both extra-chromosomal circular and linear DNA and DNA that has been incorporated into the host chromosome(s). Where a vector is being maintained by a host cell, the vector may either be stably replicated by the cells during mitosis as an autonomous structure, or is incorporated within the host's genome.

The expression vector may comprise a promoter, a ribosome binding site for translation initiation and a transcription terminator. The vector may also include appropriate sequences for amplifying expression.

The invention provides amplification primer sequence pairs for amplifying nucleic acids encoding polypeptides with a phytase activity, or subsequences thereof. One of skill in the art can design amplification primer sequence pairs for any part of or the full length of these sequences. Amplification methods are also well known in the art, and include, e.g., polymerase chain reaction, PCR; transcription amplification; self-sustained sequence replication; Q Beta replicase amplification; and other RNA polymerase mediated techniques.

"Polypeptide," as used herein comprises "amino acids" or "amino acid sequences" that are oligopeptides, peptides, polypeptides or protein sequences, or alternatively, are fragments, portions or subunits of any of these, and to naturally occurring or synthetic molecules.

In one aspect, polypeptide and peptides of the invention have phytase activity. In alternative aspects, they also can be useful as, e.g., labeling probes, antigens, toleragens, motifs, phytase active sites.

Polypeptides and peptides of the invention can be isolated, synthetic, or recombinant. Peptides and proteins can be recombinantly expressed in vitro or in vivo. The peptides and polypeptides of the invention can be made and isolated using any method known in the art. Polypeptides and peptides of the invention can also be synthesized, in whole or in part, using chemical methods well known in the art. For example, phytase polypeptides can be produced in a standard recombinant expression system (as described herein), chemically synthesized, or purified from organisms in which they are naturally expressed.

In alternative aspects, "recombinant" polypeptides or proteins of the invention include (refer to) polypeptides or proteins produced by recombinant DNA techniques; e.g., produced from cells transformed by an exogenous DNA construct encoding the desired polypeptide or protein.

In alternative aspects, peptides and polypeptides of the invention are glycosylated. The glycosylation can be added post-translationally either chemically or by cellular biosynthetic mechanisms, wherein the later incorporates the use of known glycosylation motifs, which can be native to the sequence or can be added as a peptide or added in the nucleic acid coding sequence. The glycosylation can be O-linked or N-linked, or, a combination thereof.

In alternative aspects, peptides and polypeptides of the invention, as defined above, comprise "mimetic" and "peptidomimetic" forms, either in part or completely. In one aspect, the terms "mimetic" and "peptidomimetic" refer to a synthetic chemical compound which has substantially the same structural and/or functional characteristics of the polypeptides of the invention. The mimetic can be either entirely composed of synthetic, non-natural analogues of amino acids, or, is a chimeric molecule of partly natural peptide amino acids and partly non-natural analogs of amino acids. The mimetic can also incorporate any amount of natural amino acid conservative substitutions as long as such substitutions also do not substantially alter the mimetic's structure and/or activity. As with polypeptides of the invention which are conservative variants, routine experimentation will determine whether a mimetic is within the scope of the invention, i.e., that its structure and/or function is not substantially altered. Thus, in one aspect, a mimetic composition is within the scope of the invention if it has a phytase activity.

In alternative aspects, conservative substitutions are those that substitute a given amino acid in a polypeptide by another amino acid of like characteristics. In alternative aspects, conservative substitutions are the following replacements: replacements of an aliphatic amino acid such as Ala, Val, Leu and Ile with another aliphatic amino acid; replacement of a Ser with a Thr or vice versa; replacement of an acidic residue such as Asp and Glu with another acidic residue; replacement of a residue bearing an amide group, such as Asn and Gln, with another residue bearing an amide group; exchange of a basic residue such as Lys and Arg with another basic residue; and replacement of an aromatic residue such as Phe, Tyr with another aromatic residue. substitution of one hydrophobic amino acid, such as isoleucine, valine, leucine, or methionine, for another, or substitution of one polar amino acid for another, such as substitution of arginine for lysine, glutamic acid for aspartic acid or glutamine for asparagine. In one aspect, one or more amino acids can be deleted, for example, from a phytase polypeptide of the invention to result in modification of the structure of the polypeptide without significantly altering its biological activity, or alternative, to purposely significantly alter its biological activity. For example, amino- or carboxyl-terminal amino acids that are required, or alternatively are not required, for phytase biological activity can be removed and/or added. Modified polypeptide sequences of the invention can be assayed for phytase biological activity by any number of methods, including contacting the modified polypeptide sequence with a phytase substrate and determining whether the modified polypeptide decreases the amount of specific substrate in the assay or increases the bioproducts of the enzymatic reaction of a functional phytase polypeptide with the substrate.

In one aspect, peptides and polypeptides of the invention have sequences "substantially identical" amino acid sequences of the invention, i.e., a sequence that differs by one or more conservative or non-conservative amino acid substitutions, deletions, or insertions, particularly when such a substitution occurs at a site that is not the active site of the molecule, and provided that the polypeptide essentially retains its functional properties.

In one embodiment, the phytase is selected from a group consisting of: a polypeptide having the amino acid sequence of SEQ ID NO:3 (encoded by a polynucleotide of SEQ ID NO:1 or SEQ ID NO:2); a polypeptide having the amino acid sequence of SEQ ID NO:6 (encoded by a polynucleotide of SEQ ID NO:4 or SEQ ID NO:5); and a polypeptide having the amino acid sequence of SEQ ID NO:8 (encoded by a polynucleotide of SEQ ID NO:7).

In another embodiment, the phytase is a polypeptide variant of SEQ ID NO:3, SEQ ID NO:6, or SEQ ID NO:8, wherein the polypeptide variant has an amino acid sequence having at least about 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98.0%, 98.1%, 98.2%, 98.3%, 98.4%, 98.5%, 98.6%, 98.7%, 98.8%, 98.9%, 99.0%, 99.1%, 99.2%, 99.3%, 99.4%, 99.5%, 99.6%, 99.7%, 99.8%, 99.9%, or complete (100%) identity to the polypeptide of SEQ ID NO:3, SEQ ID NO:6, or SEQ ID NO:8, or an enzymatically active fragment thereof, wherein the polypeptide variant has phytase activity.

The invention provides phytases having no or modified signal sequences (also called signal peptides (SPs), or leader peptides), or heterologous signal sequences. The polypeptides of the invention also can have no or modified or heterologous prepro domains and/or catalytic domains (CDs). The modified or heterologous SPs, prepro domains and/or CDs incorporated in a polypeptide the invention can be part of a fusion protein, e.g., as a heterologous domain in a chimeric protein, or added by a chemical linking agent. For example, an enzyme of the invention can comprise a heterologous SP and/or prepro domain in a vector, e.g., a pPIC series vector (Life Technologies, Carlsbad, Calif.).

Additionally, polypeptides of the invention can further comprise heterologous sequences, either sequences from other phytases, or from non-phytase sources, or entirely synthetic sequences. Thus, in one aspect, a nucleic acid of the invention comprises coding sequence for an endogenous, modified or heterologous signal sequence (SP), prepro domain and/or catalytic domain (CD) and a heterologous sequence (i.e., a sequence not naturally associated with the a signal sequence (SP), prepro domain and/or catalytic domain (CD) of the invention). The heterologous sequence can be on the 3' terminal end, 5' terminal end, and/or on both ends of the SP, prepro domain and/or CD coding sequence.

Immobilized enzyme and solid supports of the invention are the phytase enzymes, or fragments thereof and nucleic acids that encode the enzymes and fragments can be affixed to a solid support. This is often economical and efficient in the use of the phytases in industrial processes. For example, a consortium or cocktail of phytase enzymes (or active fragments thereof), which are used in a specific chemical reaction, can be attached to a solid support and dunked into a process vat. The enzymatic reaction can occur. Then, the solid support can be taken out of the vat, along with the enzymes affixed thereto, for repeated use. In one embodiment of the invention, an isolated nucleic acid of the invention is affixed to a solid support. In another embodiment of the invention, the solid support is selected from the group of a gel, a resin, a polymer, a ceramic, a glass, a microelectrode, and/or any combination thereof.

There are many methods that would be known to one of skill in the art for immobilizing enzymes or fragments thereof, or nucleic acids, onto a solid support. Some examples of such methods include, e.g., electrostatic droplet generation, electrochemical means, via adsorption, via covalent binding, via cross-linking, via a chemical reaction or process, via encapsulation, via entrapment, via calcium alginate, or via poly (2-hydroxyethyl methacrylate). Like methods are described in Methods in Enzymology, Immobilized Enzymes and Cells, Part C. 1987. Academic Press. Edited by S. P. Colowick and N. O. Kaplan. Volume 136; and Immobilization of Enzymes and Cells. 1997. Humana Press. Edited by G. F. Bickerstaff. Series: Methods in Biotechnology, Edited by J. M. Walker.

"Variant," as used herein includes derivatives or analogs of these polypeptides. In particular, the variants may differ in amino acid sequence from the polypeptides of the invention, and sequences substantially identical thereto, by one or more substitutions, additions, deletions, fusions, and truncations, which may be present in any combination.

Methods of generating variants of the nucleic acids of the invention, e.g., those encoding a phytase enzyme are well known in the art. These methods can be repeated or used in various combinations to generate phytase enzymes having an altered or different activity or an altered or different stability from that of a phytase encoded by the template nucleic acid. These methods also can be repeated or used in various combinations, e.g., to generate variations in gene/message expression, message translation or message stability. In another aspect, the genetic composition of a cell is altered by, e.g., modification of a homologous gene ex vivo, followed by its reinsertion into the cell.

The invention also provides methods for changing the characteristics of a phytase of the invention by mutagenesis and other methods, including, e.g., the proprietary approaches developed by Verenium Corporation (previously Diversa Corporation, San Diego, Calif.), e.g., GeneReassembly (see, e.g., U.S. Pat. No. 6,537,776; Gene Site Saturation Mutagenesis (GSSM) (see, e.g., U.S. Pat. Nos. 6,171,820 and 6,764,835), Exonuclease-Mediated Gene Assembly in Directed Evolution (see, e.g., U.S. Pat. Nos. 6,361,974 and 6,352,842), End Selection in Directed Evolution (see, e.g., U.S. Pat. Nos. 6,358,709 and 6,238,884), Recombination-Based Synthesis Shuffling (see, e.g., U.S. Pat. Nos. 5,965,408 and 6,440,668, and Australian Patent No. AU724521), Directed Evolution of Thermophilic Enzymes (see, e.g., U.S. Pat. Nos. 5,830,696 and 6,335,179), and Tailored Multi-site combinatorial assembly (see, e.g., WO 2009/018449).

Various techniques known in molecular biology can be used, e.g., random PCR mutagenesis, see, e.g., Rice (1992) Proc. Natl. Acad. Sci. USA 89:5467-5471; or, combinatorial multiple cassette mutagenesis, see, e.g., Crameri (1995) Biotechniques 18:194-196. Alternatively, nucleic acids, e.g., genes, can be reassembled after random, or "stochastic,"

fragmentation, see, e.g., U.S. Pat. Nos. 6,291,242; 6,287,862; 6,287,861; 5,955,358; 5,830,721; 5,824,514; 5,811,238; 5,605,793. In alternative aspects, modifications, additions or deletions are introduced by error-prone PCR, shuffling, oligonucleotide-directed mutagenesis, assembly PCR, sexual PCR mutagenesis, in vivo mutagenesis, cassette mutagenesis, recursive ensemble mutagenesis, exponential ensemble mutagenesis, site-specific mutagenesis, gene reassembly, gene site saturation mutagenesis (GSSM), synthetic ligation reassembly (SLR), recombination, recursive sequence recombination, phosphothioate-modified DNA mutagenesis, uracil-containing template mutagenesis, gapped duplex mutagenesis, point mismatch repair mutagenesis, repair-deficient host strain mutagenesis, chemical mutagenesis, radiogenic mutagenesis, deletion mutagenesis, restriction-selection mutagenesis, restriction-purification mutagenesis, artificial gene synthesis, ensemble mutagenesis, chimeric nucleic acid multimer creation, and/or a combination of these and other methods.

"Transgenic Plants and Seeds" as used herein comprise a nucleic acid, a polypeptide, an expression cassette, cloning mechanism or vector of the invention, or a transfected or transformed cell of the invention. The invention also provides plant products, e.g., oils, seeds, leaves, extracts and the like, comprising a nucleic acid and/or a polypeptide of the invention. The transgenic plant can be dicotyledonous (a dicot) or monocotyledonous (a monocot). The invention also provides methods of making and using these transgenic plants and seeds. The transgenic plant or plant cell expressing a polypeptide of the present invention may be constructed in accordance with any method known in the art. See, for example, U.S. Pat. No. 6,309,872.

In some embodiments, to achieve extracellular expression of the phytase, the expression construct of the present invention utilizes a secretory signal sequence. Although signal sequences which are homologous (native) to the plant host species, heterologous signal sequences, i.e. those originating from other plant species or of microbial origin, may be used as well, such signal sequences are known to those skilled in the art. Appropriate signal sequences which may be used within the context of the present invention are disclosed in Blobel et al., 1979; Von Heijne, 1986; Garcia et al., 1987; Sijmons et al., 1990; Ng et al., 1994; and Powers et al., 1996).

"Transgenic non-human animals" as used herein are a nucleic acid, a polypeptide, an expression cassette or vector or a transfected or transformed cell of the invention. The transgenic non-human animals can be, e.g., goats, rabbits, sheep, pigs, cows, rats and mice, comprising the nucleic acids of the invention. These animals can be used, e.g., as in vivo models to study phytase activity, or, as models to screen for modulators of phytase activity in vivo. The coding sequences for the polypeptides to be expressed in the transgenic non-human animals can be designed to be constitutive, or, under the control of tissue-specific, developmental-specific or inducible transcriptional regulatory factors. Transgenic non-human animals can be designed and generated using any method known in the art.

In one embodiment, a phytase of the invention is used as an additive for animal feed. Some of the benefits of adding phytase include but are not limited to: increasing the total phosphorus contained in feed, reducing phosphorus released into environment via excretion, and increasing digestibility of other minerals and amino acids.

In another embodiment, an animal feed or a supplement comprising a phytase of the invention can be given to any animal. Phytase is commonly included in animal feed for poultry such as chickens, broilers, or laying hens; turkeys; ducks; swine such as pigs, piglets, or sows; bovine such as cattle; and aquaculture feeds for fish such as trout, salmon, tilapia, catfish, and bass.

In another embodiment, an animal feed comprising a Phytase of the invention can be provided to an animal in any formulation known to those skilled in the art. Examples of animal feed formulations include, but are not limited to: a delivery matrix, a pellet, a tablet, a gel, a liquid, a spray, ground grain, or a powder.

In another embodiment, a phytase of the invention is used to treat individuals predisposed to bone loss such as osteoporosis, cachexia, and medical treatments, such as chemotherapies, that can compromise the proper uptake or utilization of nutrients. One aspect of the invention is to provide a pharmaceutical or dietary formulation comprising a phytase. It is also common in the art to use a phytase of this invention for individuals undergoing athletic training, intense physical training, hospital diets, micronutrient-poor cereal and legume diets, school lunch programs or any other nutritional program.

In one embodiment, a phytase of the invention is used in the industrial production of biofuels and biomass conversion. For example, phytase is used in fermentation or alcohol production processes. In one embodiment, the alcohol is ethanol, which may be for fuel use or is potable ethanol. In one embodiment, the fermentation process may utilize starch or a non-starch plant material, such as a lignocellulosic material, such as cellulose, hemicellulose, and/or lignin.

In another embodiment, a phytase of the invention is used to treat distillers dried soluble (DDS); distillers dried grains (DDG); condensed distillers soluble (CDS); distillers wet grains (DWG); and distillers dried grains with soluble (DDGS). These byproducts of the alcohol fermentation process can be used as an ingredient for animal feed. In another embodiment, the phytase is used to reduce scaling, and increase ethanol yield.

In another embodiment, a phytase of the invention is used to convert algae, virgin vegetable oils, waste vegetable oils, sewage into fuel.

EXAMPLES

Example 1: Phytase Specific Activity

Specific activity was determined (as described below) for phytases expressed in *Pseudomonas* and in *Pichia*. The specific activities of the phytase molecules were not impacted by expression in the two analyzed expression systems (see FIG. 1). The *Pichia* cells were removed from the fermentation broth by centrifugation and the supernatant was DNAse treated and buffer exchanged with 100 mM TRIS, pH 8.0. *Pseudomonas* cells expressing phytase were lysed using a microfluidizer and centrifuged. The supernatant was DNAse treated and buffer exchanged with 100 mM Tris pH 8.0. The samples were then loaded onto an ion exchange column (FPLC) and fractions were collected. Eluted fractions were tested for activity and run on an SDS-PAGE; pure fractions were pooled.

Protein concentration was determined via spectrophotometry (absorbance at 280 nm). The specific protein absorption coefficient (280 nm) was determined using the peptide based software calculator, VECTOR NTI (Life Technologies, Carlsbad, Calif.). The 280 nm coefficient for the phytase molecules based on the peptide sequence was determined to be $OD_{280}$ 1.0=0.875 mg/mL (SEQ ID NO:6 (encoded by SEQ ID NO:4), SEQ ID NO:6 (encoded by SEQ ID NO:5), SEQ ID NO:3 (encoded by SEQ ID NO:1) and SEQ ID NO:3 (encoded by SEQ ID NO:2) and 0.897 mg/mL (SEQ ID NO:8, encoded by SEQ ID NO:7). DNA was determined to be below measurable values based on absorbance ratios (260/280 nm).

Phytase specific activity was determined using a colorimetric assay which detects free phosphate from the dephosphorylation of phytic acid. An aliquot of 50 µL of purified phytase was added to preheated (37° C.) 950 µL substrate mix (4 mM dodecasodium phytate 100 mM Na-acetate pH 5.5). Aliquots of 50 uL were withdrawn every minute and quenched in 50 µL color/stop solution (Molybdate-Vanadate). After 10 minutes, when the yellow color had completely developed, a SpectraMax Plus absorbance reader was used to measure $OD_{415}$. Activity was determined by the calculations illustrated bellow.

$$\text{Activity} = \frac{\text{slope of reaction curve } (A_{415\,nm}\text{min}^{-1}) \times \text{dilution factor} \times 20}{\text{slope of Phosphate } std \text{ curve } (A_{415\,nm}\mu\text{mol/mL Phosphate})}$$

$$= \frac{\mu\text{mol Phosphate}}{\text{min} * \text{mL}}$$

$$= \text{Units/mL}$$

$$\text{Specific Activity} = \frac{\text{Units/mL}}{\text{Phytase mg/mL}}$$

One unit is defined as the # µmoles of phosphate released per minute by the enzyme

Example 2: Phytase Activity at High Temperature (DSC Tm)

Figure 2:
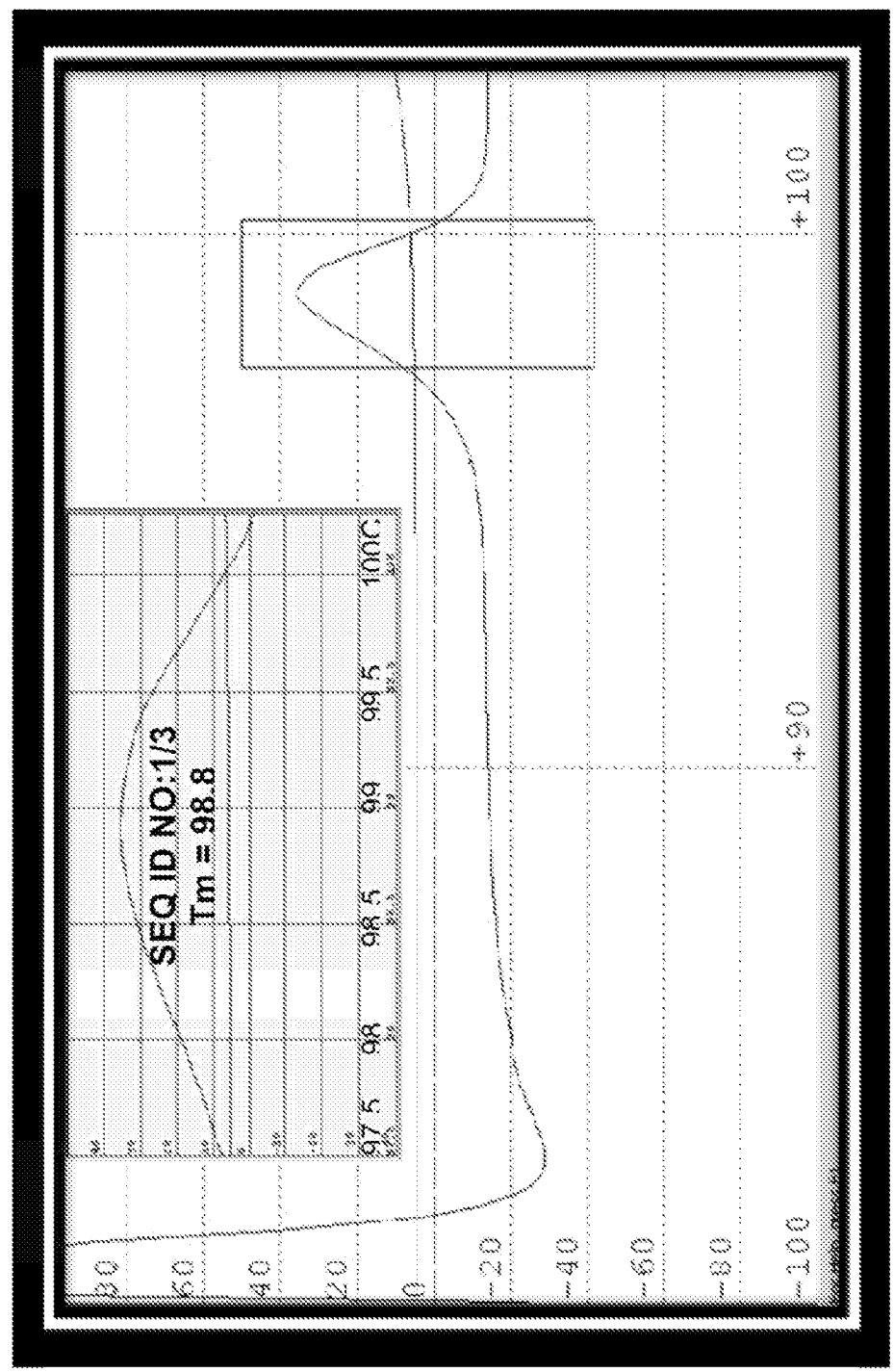
FIG. 2: DSC chromatogram for phytase SEQ ID NO:3 (encoded by SEQ ID NO:1) in 100 mM Citrate pH 5.5+10% Sorbitol-10% NaCl.
Figure 3:
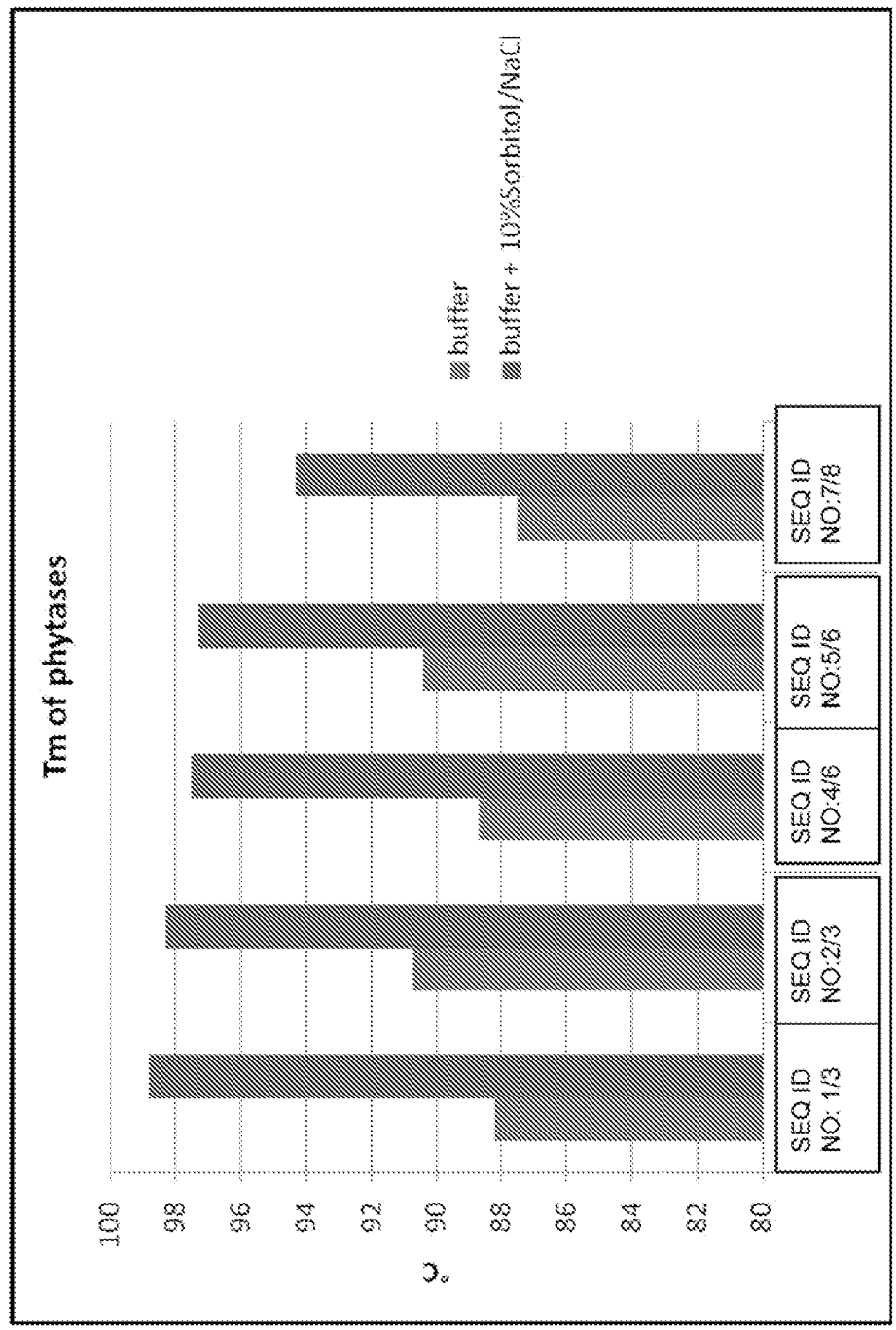
FIG. 3: DSC $T_m$ values (° C.) for phytase in 100 mM Citrate pH 5.5 with and without 10% Sorbitol-10% NaCl. SEQ ID NO:3 (encoded by SEQ ID NO:1) and SEQ ID NO:6 (encoded by SEQ ID NO:4) are *Pseudomonas* expressed. SEQ ID NO:3 (encoded by SEQ ID NO:2), SEQ ID NO:6 (encoded by SEQ ID NO:5), and SEQ ID NO:8 (encoded by SEQ ID NO:7) are *Pichia* expressed.

To determine the thermostability of the phytases a Perkin-Elmer Pyris 1 Differential Scanning calorimeter (DSC) was employed to determine melting temperatures ($T_m$) of the phytase variants. The $T_m$ analysis was performed at pH 5.5 (similar to an aqueous feed extract) using 100 mM Citrate as buffer. DSC runs were run with or without 10% Sorbitol-10% NaCl. DSC analysis indicates that 10% Sorbitol-10% NaCl improved the thermostability of the phytases. In liquid form, $T_m$ greater than 98° C. can be achieved (FIG. 2). Pseudomonas-expressed phytases showed ~1-2° C. lower $T_m$ than the Pichia-expressed phytases in buffer alone, however this temperature reduction was not observed when 10% Sorbitol-10% NaCl was added (FIG. 3).

Example 3: pH Profile

Figure 4:
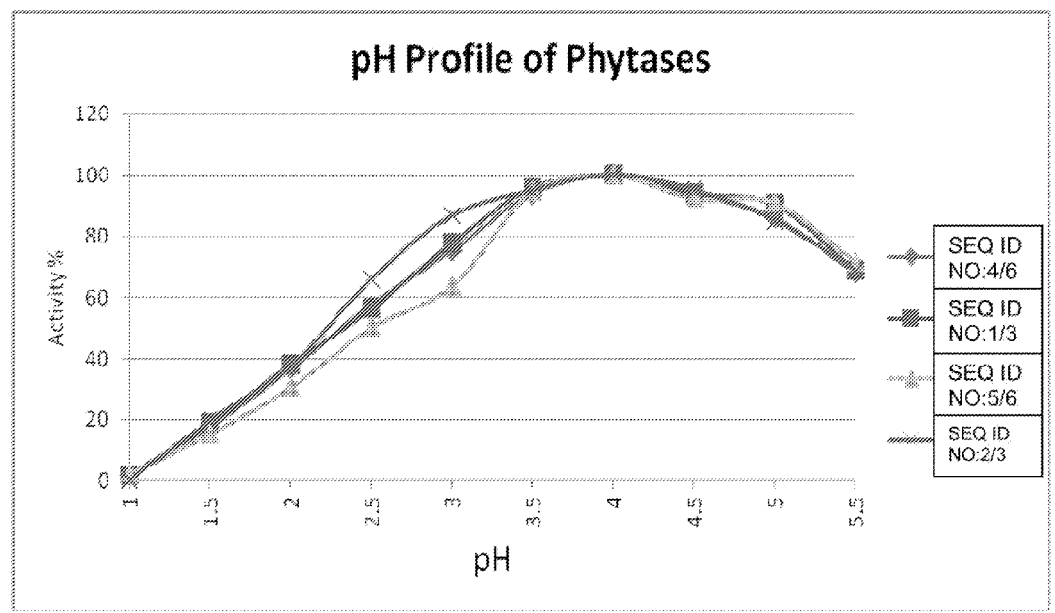
FIG. 4: pH profile of phytases using Britton-Robinson "universal" buffer on 4 mM phytate. SEQ ID NO:3 (encoded by SEQ ID NO:1) and SEQ ID NO:6 (encoded by SEQ ID NO:4) are *Pseudomonas* expressed. SEQ ID NO:3 (encoded by SEQ ID NO:2) and SEQ ID NO:6 (encoded by SEQ ID NO:5) are *Pichia* expressed.

The pH optimums of the phytases, when expressed in Pichia or Pseudomonas (FIG. 4), were determined to be pH 3.5-pH 4.5. Activity of the phytases on the phytic substrate at different pH points were determined using the Britton-Robinson buffer in order to remove confounding variables which result from switching buffers to cover the tested range of pH 1.0-pH 5.5. The activities at different pHs were normalized to the pH optimum of 4.

Figure 5:
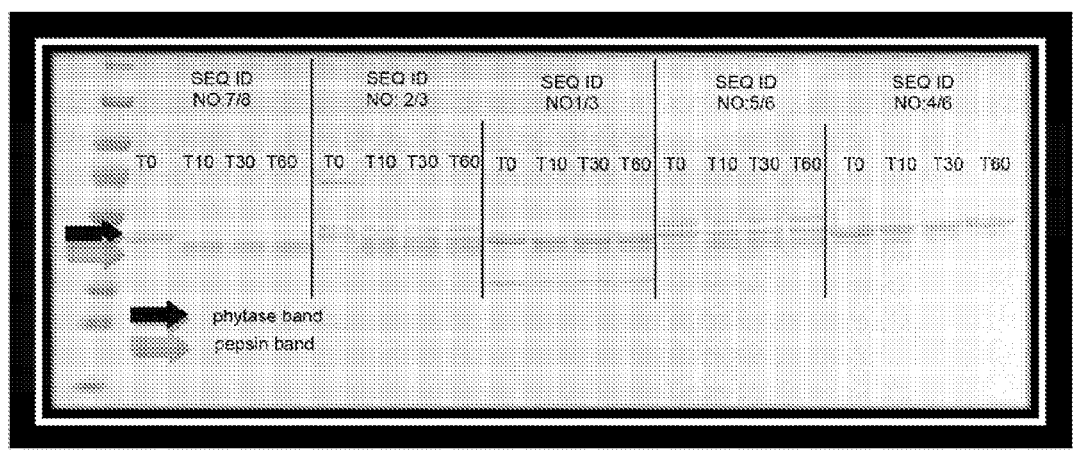
FIG. 5: SDS-PAGE of phytases treated to SGF+pepsin. SEQ ID NO:3 (encoded by SEQ ID NO:1) and SEQ ID NO:6 (encoded by SEQ ID NO:4) are *Pseudomonas* expressed. SEQ ID NO:3 (encoded by SEQ ID NO:2), SEQ ID NO:6 (encoded by SEQ ID NO:5), and SEQ ID NO:8 (encoded by SEQ ID NO:7) are *Pichia* expressed.

Example 4: Phytase Activity at Low pH (Simulated Gastric Fluid (SGF)) Conditions, and pH Profiles Gastric stability was assessed by treating the phytase molecules in a simulated gastric fluid (SGF) at pH 1.2 over a time course of 60 minutes. Pepsin was added to the SGF at 10 pepsin units per µg phytase. At 10, 30 and 60 minutes, aliquots of the SGF-phytase mixture were removed and quenched in 200 mM Na-Carbonate buffer pH 11.0. Samples were then analyzed by SDS-PAGE to determine the extent of protein digestion. The SDS-PAGE (FIG. 5) results demonstrated that the phytase band for SEQ ID NO:8 (encoded by SEQ ID NO:7) molecule degrades within 10 minutes SGF+pepsin treatment. The other phytase molecules expressed in Pichia (SEQ ID NO:3 (encoded by SEQ ID NO:2) and SEQ ID NO:6 (encoded by SEQ ID NO:5)) and Pseudomonas (SEQ ID NO:3 (encoded by SEQ ID NO:1) and SEQ ID NO:6 (encoded by SEQ ID NO:4)) show minimal degradation after 60 minutes.

Figure 6:
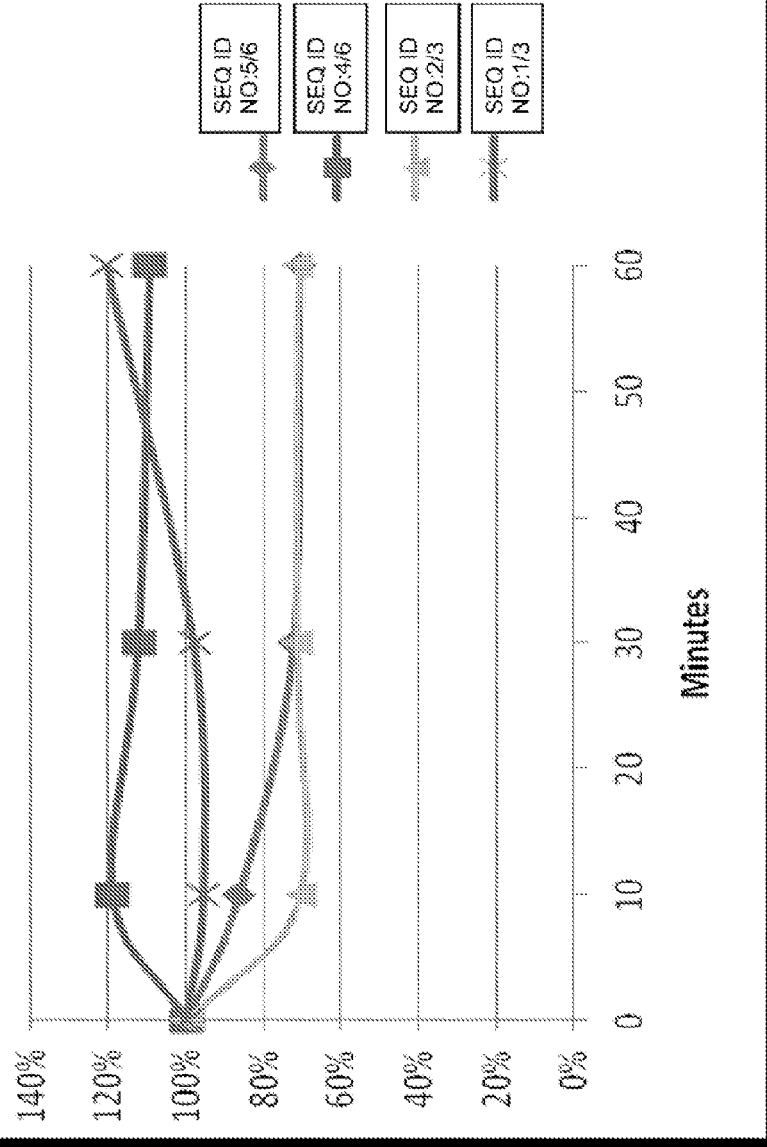
FIG. 6: Activity of thermostable phytases after SGF treatment. Minimal or no loss in activity is observed for thermostable phytases. T0 sample was pre-quenched with the pH 11 buffer prior to the addition of the phytase enzyme.

Based on previous reports, the E. coli wt appA phytase demonstrated an SGF half life of 2.4 minutes (Garrett et al, 2004). The phytase of SEQ ID NO:8 (encoded by SEQ ID NO:7) has practically no activity after 10 minutes and the other phytases (SEQ ID NO:3 (encoded by SEQ ID NO:2), SEQ ID NO:6 (encoded by SEQ ID NO:5), (SEQ ID NO:3 (encoded by SEQ ID NO:1), and SEQ ID NO:6 (encoded by SEQ ID NO:4)) maintain an intact protein (FIG. 5) and activity after 60 minutes (FIG. 6).

Example 5: Phytase Expression

Pichia expression system utilizes the Pichia pastoris GS 115 strain and methanol inducible promoter (AOX) licensed from RCT. Phytase is secreted into the fermentation broth. The phytase of SEQ ID NO:3 (encoded by SEQ ID NO:2) expressed in Pichia was tested in 30 L fermenters and achieved 7.0 g/L after 120 hrs. The fermentation results of phytase SEQ ID NO:6 (encoded by SEQ ID NO:5) were less than 7.0 g/L.

Figure 7:
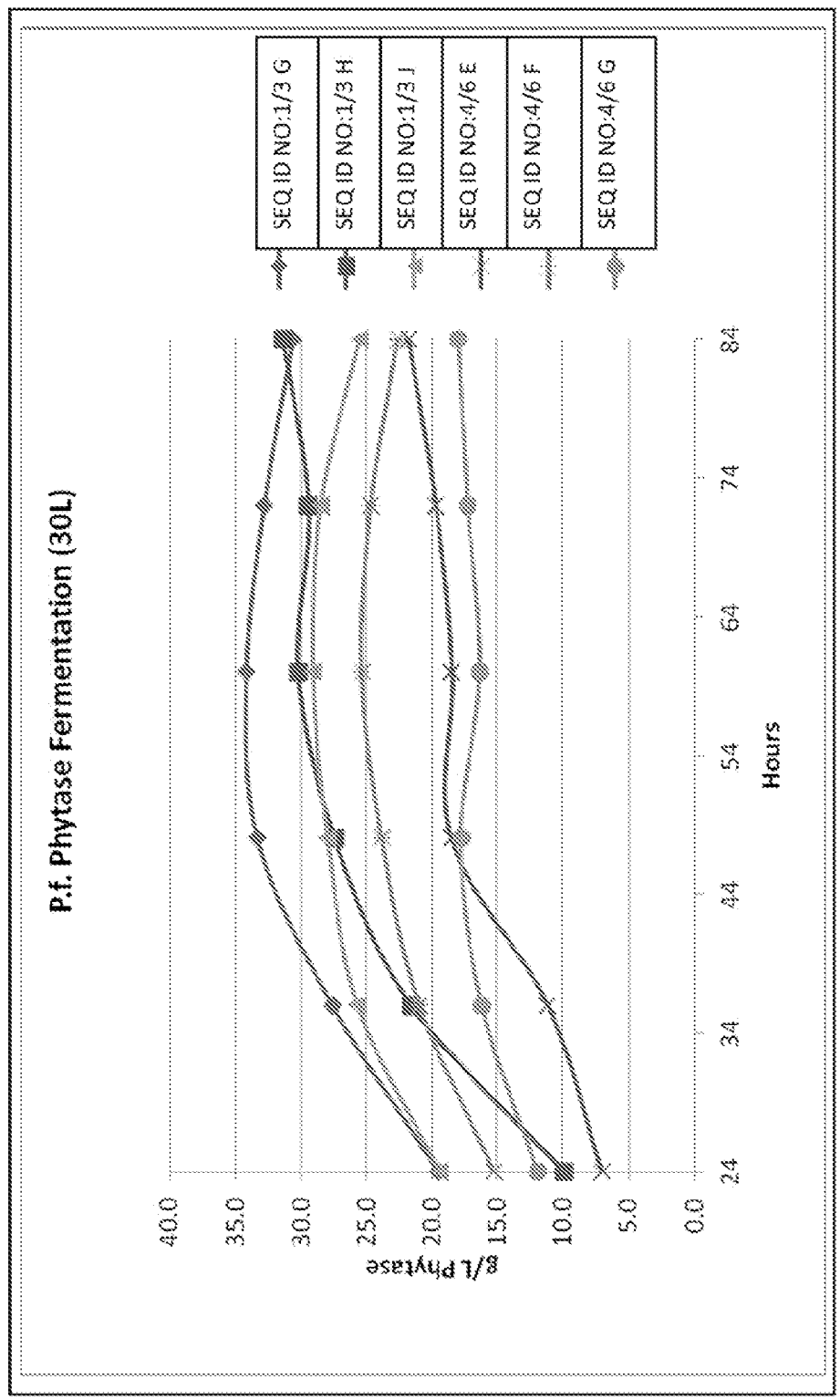
FIG. 7: *Pseudomonas* (P.f.) expression levels of the phytase fermentation (30 L).

Pseudomonas expression system from DOW utilizes strain (DC454) with the phytase sequence inserted to the pDOW1169 (inducible by IPTG). Phytase is expressed intracellular and therefore requires cell lysis for phytase recovery (See FIG. 7). The results, in triplicate, for intracellular phytase (SEQ ID NO:3 (encoded by SEQ ID NO:1) and SEQ ID NO:6 (encoded by SEQ ID NO:4)) expression in Pseudomonas range from about 5 g/L to about 35.0 g/L.

What is claimed is:

1. An isolated, recombinant, or synthetic polypeptide comprising the amino acid sequence SEQ ID NO:3.

2. An isolated, recombinant, or synthetic nucleic acid comprising
    (a) a nucleic acid sequence selected from a group consisting of SEQ ID NO:1 and SEQ ID NO:2, wherein the nucleic acid sequence encodes a polypeptide having a phytase activity, or
    (b) a nucleic acid sequence of SEQ ID NO:1, wherein the nucleic acid sequence encodes a polypeptide having a phytase activity and the polypeptide comprises an amino acid sequence of SEQ ID NO:3.

3. A composition comprising the isolated, recombinant, or synthetic polypeptide of claim 1.

4. The composition of claim 3, wherein the composition is:
    (a) a food or a feed,
    (b) a food additive, a feed additive or a dietary supplement, or
    (c) a pharmaceutical.

5. The isolated, recombinant, or synthetic nucleic acid of claim 2, wherein:
    the nucleic acid sequence of SEQ ID NO:1 encodes a polypeptide having a phytase activity, and wherein the polypeptide is produced in a recombinant *Pseudomonas fluorescens* expression system.

6. The isolated, recombinant, or synthetic nucleic acid of claim 2, wherein the nucleic acid sequence of SEQ ID NO:2 encodes a polypeptide having a phytase activity, wherein the polypeptide is produced in a recombinant *Pichia pastoris* expression system.

7. The isolated, recombinant, or synthetic polypeptide of claim 1, wherein the polypeptide has phytase activity and is produced via intracellular expression system.

8. The isolated, recombinant, or synthetic nucleic acid of claim 2, wherein the phytase encoded by the nucleic acid sequence is expressed intracellularly at a level of at least 7.0 g/L, 8.0 g/L, 9.0 g/L, 10.0 g/L, 11.0 g/L, 12.0 g/L, 13.0 g/L, 14.0 g/L, 15.0 g/L, 16.0 g/L, 17.0 g/L, 18.0 g/L, 19.0 g/L, 20.0 g/L, 21.0 g/L, 22.0 g/L, 23.0 g/L, 24.0 g/L, 25.0, g/L, 26.0 g/L, 27.0 g/L, 28.0 g/L, 29.0 g/L, 30.0 g/L, 31.0 g/L, 32.0 g/L, 33.0 g/L, 34.0 g/L, 35.0 g/L, 36 g/L, 37 g/L, 38 g/L, 39 g/L, or 40 g/L.

9. The phytase of claim 7 or 8, wherein
    (a) the intracellular expression is in a gram-negative bacterium,
    (b) the intracellular expression of (a), wherein the gram-negative bacterium is a *Pseudomonas* species, *E. coli* species, *Ralstonia* species, or *Caulobacter* species, or
    (c) the intracellular expression of (a), wherein the gram-negative bacterium is a *Pseudomonas fluorescens* species.

10. The phytase of claim 9, wherein the phytase is derived from an *E. coli*, a *Bacillus* sp., a *Hafnia* sp., *Perniophora lycii*, a *Buttiauxella* sp., a *Citrobacter* sp., or *Aspergillus niger*.

11. The isolated, recombinant, or synthetic polypeptide of claim 1, wherein the polypeptide
   (a) does not comprise an endogenous, modified, or heterologous signal sequence, a proprotein sequence, or any combination thereof, or
   (b) further comprises a heterologous amino acid sequence selected from the group consisting of: a signal sequence, a tag, an epitope, an N-terminal extension, a C-terminal extension, and any combination thereof.

12. The isolated, recombinant, or synthetic polypeptide of claim 1, wherein the polypeptide
   (a) further comprises at least a second enzyme, or
   (b) the polypeptide of (a), wherein the second enzyme is selected from the group consisting of: a lactase, a lipase, a protease, a catalase, a xylanase, a cellulase, a glucanase, a mannanase, an amylase, an amidase, an epoxide hydrolase, an esterase, phospholipase, transaminase, an amine oxidase, cellobiohydrolase, an ammonia lyase, and any combination thereof.

13. The isolated, recombinant, or synthetic polypeptide of claim 1, wherein the phytase:
   (a) has a specific activity from about 1000 U/mg to 1,600 U/mg,
   (b) is active at a pH from at least pH 1.0 to about pH 9.0, or
   (c) is active at a temperature from about 50 degrees C. to about 100 degrees C.

* * * * *

SEQUENCE LISTING

```
<160> NUMBER OF SEQ ID NOS: 8

<210> SEQ ID NO 1
<211> LENGTH: 1239
<212> TYPE: DNA
<213> ORGANISM: Artificial Sequence
<220> FEATURE:
<223> OTHER INFORMATION: Synthetically generated polynucleotide

<400> SEQUENCE: 1
```

```
atgcagagcg agccggagct gaagctggaa agcgtggtga ttgtcagccg tcatggtgtg      60
cgtgctccaa ccaaggctac gcaactgatg caggatgtca ccccagacgc atggccaacc     120
tggccggtaa aactgggtga gctgacaccg cgcggtggtg agctaatcgc ctatctcgga     180
cattactggc gtcagcgtct ggtagccgac ggattgctgc ctaaagaagg ctgcccgcag     240
tctggtcagg tcgcgattat tgctgatgtc gacgagcgta cccgtaaaac aggcgaagcc     300
ttcgccgccg gctggcacc tgactgtgca ataaccgtac atcatcaggc agatacgtcc     360
agtcccgatc cgttatttaa tcctctaaaa actggcgttt gccaactgga tgtcgcgaac     420
gtgagacggg cgatcctcag aagggcagga gggtcaattg ctgactttac ccggcattat     480
caaacggcgt ttcgcgaact ggaacgggtg cttaattttc gcaatcaaa cttgtgcctt      540 aaacgtgaga acaggacga aagctgttca ttaacgcagg cattaccatc ggaactcaag     600
gtgagcgccg acgatgtctc attaaccggt gcggttagcc tcgcatcaat gctgacggag     660
atatttctcc tgcaacaagc acagggaatg ccggagccgg gtggggaag gatcaccgat     720 tcacaccagt ggaacaccct gctaagtttg cataacgcgg tgtttgattt gctacaacgc     780
acgccagagg ttgcccgcag ccgcgccacc ccgttattag atttgatcaa dacagcgttg     840
acgccccatc caccgcaaaa acaggcgtat ggtgtgacat acccacttc agtgctgttt     900 atcgccggac acgatactaa tctggcaaat ctcggcggcg cactggagct caactggacg     960
cttcccggtc agccggataa ctatccgcca ggtggtgaac tggtgtttga acgctggcgt    1020
cggctaagcg ataacagcca gtggattcag gtttcgctgg tcttccagac tttacagcag    1080
atgcgtgata aaacgccgct gtcattaaat acgccgcccg gagaggtgaa actgaccctg    1140
gcaggatgtg aagagcgaaa tgcgcagggc atgtgttcgt tggcaggttt tacgcaaatc    1200
gtgaatgaag cacgcatacc ggcgtgcagt ttgtgatga                            1239
```

<210> SEQ ID NO 2
<211> LENGTH: 1230
<212> TYPE: DNA
<213> ORGANISM: Artificial Sequence
<220> FEATURE:
<223> OTHER INFORMATION: Synthetically generated polynucleotide

<400> SEQUENCE: 2

```
cagagtgagc cggagctgaa gctggaaagt gtggtgattg tcagtcgtca tggtgtgcgt      60
gctccaacca aggctacgca actgatgcag gatgtcaccc cagacgcatg gccaacctgg     120
ccggtaaaac tgggtgagct gacaccgcgc ggtggtgagc taatcgccta tctcggacat     180
tactggcgtc agcgtctggt agccgacgga ttgctgccta agaaggctg cccgcagtct     240 ggtcaggtcg cgattattgc tgatgtcgac gagcgtaccc gtaaaacagg cgaagccttc     300
gccgccgggc tggcacctga ctgtgcaata accgtacatc atcaggcaga tacgtccagt     360
cccgatccgt tatttaatcc tctaaaaact ggcgtttgcc aactggatgt cgcgaacgtg     420
agacgggcga tcctcagaag gcaggaggg tcaattgctg actttacccg gcattatcaa      480
acggcgtttc gcgaactgga acgggtgctt aattttccgc aatcaaactt gtgccttaaa     540
cgtgagaaac aggacgaaag ctgttcatta acgcaggcat taccatcgga actcaaggtg     600
agcgccgacg atgtctcatt aaccggtgcg gttagcctcg catcaatgct gacggagata     660
tttctcctgc aacaagcaca gggaatgccg gagccggggt ggggaaggat caccgattca    720
caccagtgga acaccttgct aagtttgcat aacgcggtgt ttgatttgct acaacgcacg    780
```

```
ccagaggttg cccgcagccg cgccaccccg ttattagatt tgatcaagac agcgttgacg    840
ccccatccac cgcaaaaaca ggcgtatggt gtgacattac ccacttcagt gctgtttatc    900
gccggacacg atactaatct ggcaaatctc ggcggcgcac tggagctcaa ctggacgctt    960
cccggtcagc cggataacta tccgccaggt ggtgaactgg tgtttgaacg ctggcgtcgg   1020
ctaagcgata acagccagtg gattcaggtt tcgctggtct tccagacttt acagcagatg   1080
cgtgataaaa cgccgctgtc attaaatacg ccgcccggag aggtgaaact gaccctggca   1140
ggatgtgaag agcgaaatgc gcagggcatg tgttcgttgg caggttttac gcaaatcgtg   1200
aatgaagcac gcataccggc gtgcagtttg                                    1230
```

<210> SEQ ID NO 3
<211> LENGTH: 411
<212> TYPE: PRT
<213> ORGANISM: Artificial Sequence
<220> FEATURE:
<223> OTHER INFORMATION: Synthetically generated polypeptide

<400> SEQUENCE: 3

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285
```

```
Ala Tyr Gly Val Thr Leu Pro Thr Ser Val Leu Phe Ile Ala Gly His
            290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410
```

<210> SEQ ID NO 4
<211> LENGTH: 1266
<212> TYPE: DNA
<213> ORGANISM: Artificial Sequence
<220> FEATURE:
<223> OTHER INFORMATION: Synthetically generated polynucleotide

<400> SEQUENCE: 4

```
atgcagagcg agccggagct gaagctggaa agcgtggtga ttgtcagtcg tcatggtgtg      60
cgtgctccaa ccaaggctac gcaactgatg caggatgtca ccccagacgc atggccaacc    120
tggccggtaa aactgggtga gctgacaccg cgcggtggtg agctaatcgc ctatctcgga    180
cattactggc gtcagcgtct ggtagccgac ggattgctgc taaagaagg ctgcccgcag    240
tctggtcagg tcgcgattat tgctgatgtc gacgagcgta cccgtaaaac aggcgaagcc    300
ttcgccgccg ggctggcacc tgactgtgca ataaccgtac atcatcaggc agatacgtcc    360
agtcccgatc cgttatttaa tcctctaaaa actggcgttt gccaactgga tgtcgcgaac    420
gtgactcggg cgatcctcag aagggcagga gggtcaattg ctgactttac ccggcattat    480
caaacggcgt ttcgcgaact ggaacgggtg cttaattttc gcaatcaaa cttgtgcctt    540
aaacgtgaga acaggacga agctgttca ttaacgcagg cattaccatc ggaactcaag    600
gtgagcgccg acgatgtctc attaaccggt gcggttagcc tcgcatcaat gctgacggag    660
atatttctcc tgcaacaagc acagggaatg ccggagccgg ggtggggaag gatcaccgat    720
tcacaccagt ggaacaccct gctaagtttg cataacgcgg tgtttgattt gctacaacgc    780
acgccagagg ttgcccgcag ccgcgccacc ccgttattag atttgatcaa gacagcgttg    840
acgccccatc caccgcaaaa acaggcgtat ggtgtgacat acccacttc agtgctgttt    900
atcgccggac acgatactaa tctggcaaat tcggcggcg cactggagct caactggacg    960
cttcccggtc agccggataa ctatccgcca ggtggtgaac tggtgtttga acgctggcgt   1020
cggctaagcg ataacagcca gtggattcag gtttcgctgg tcttccagac tttacagcag   1080
atgcgtgata aacgccgct gtcattaaat acgccgcccg gagaggtgaa actgaccctg   1140
gcaggatgtg aagagcgaaa tgcgcagggc atgtgttcgt tggcaggttt tacgcaaatc   1200
gtgaatgaag cacgcatacc ggcgtgcagt ttgtgatgac tcgagcccaa aacgaaaggc   1260
tcagtc                                                               1266
```

<210> SEQ ID NO 5
<211> LENGTH: 1230
<212> TYPE: DNA
<213> ORGANISM: Artificial Sequence
<220> FEATURE:
<223> OTHER INFORMATION: Synthetically generated polynucleotide

<400> SEQUENCE: 5

```
cagagtgagc cggagctgaa gctggaaagt gtggtgattg tcagtcgtca tggtgtgcgt      60
gctccaacca aggctacgca actgatgcag gatgtcaccc cagacgcatg gccaacctgg     120
ccggtaaaac tgggtgagct gacaccgcgc ggtggtgagc taatcgccta tctcggacat     180
tactggcgtc agcgtctggt agccgacgga ttgctgccta agaaggctg cccgcagtct      240 ggtcaggtcg cgattattgc tgatgtcgac gagcgtaccc gtaaaacagg cgaagccttc     300
gccgccgggc tggcacctga ctgtgcaata accgtacatc atcaggcaga tacgtccagt     360
cccgatccgt tatttaatcc tctaaaaact ggcgtttgcc aactggatgt cgcgaacgtg     420
actcgggcga tcctcagaag ggcaggaggg tcaattgctg actttacccg gcattatcaa     480
acggcgtttc gcgaactgga cgggtgcctt aattttccgc aatcaaactt gtgccttaaa     540
cgtgagaaac aggacgaaag ctgttcatta acgcaggcat taccatcgga actcaaggtg     600
agcgccgacg atgtctcatt aaccggtgcg gttagcctcg catcaatgct gacggagata     660
tttctcctgc aacaagcaca gggaatgccg gagccgggt ggggaaggat caccgattca      720
caccagtgga acaccttgct aagtttgcat aacgcggtgt ttgatttgct acaacgcacg     780
ccagaggttg cccgcagccg cgccaccccg ttattagatt tgatcaagac agcgttgacg     840
ccccatccac cgcaaaaaca ggcgtatggt gtgacattac ccacttcagt gctgtttatc     900
gccggacacg atactaatct ggcaaatctc ggcggcgcac tggagctcaa ctggacgctt     960
cccggtcagc cggataacta tccgccaggt ggtgaactgg tgtttgaacg ctggcgtcgg    1020
ctaagcgata acagccagtg gattcaggtt tcgctggtct tccagacttt acagcagatg    1080
cgtgataaaa cgccgctgtc attaaatacg ccgcccggag aggtgaaact gaccctggca    1140
ggatgtgaag agcgaaatgc gcagggcatg tgttcgttgg caggttttac gcaaatcgtg    1200
aatgaagcac gcataccggc gtgcagtttg                                     1230
```

<210> SEQ ID NO 6
<211> LENGTH: 411
<212> TYPE: PRT
<213> ORGANISM: Artificial Sequence
<220> FEATURE:
<223> OTHER INFORMATION: Synthetically generated polypolypeptide

<400> SEQUENCE: 6

```
Met Gln Ser Glu Pro Glu Leu Lys Leu Glu Ser Val Val Ile Val Ser
1               5                   10                  15

Arg His Gly Val Arg Ala Pro Thr Lys Ala Thr Gln Leu Met Gln Asp
            20                  25                  30

Val Thr Pro Asp Ala Trp Pro Thr Trp Pro Val Lys Leu Gly Glu Leu
        35                  40                  45

Thr Pro Arg Gly Gly Glu Leu Ile Ala Tyr Leu Gly His Tyr Trp Arg
    50                  55                  60

Gln Arg Leu Val Ala Asp Gly Leu Leu Pro Lys Glu Gly Cys Pro Gln
65                  70                  75                  80

Ser Gly Gln Val Ala Ile Ile Ala Asp Val Asp Glu Arg Thr Arg Lys
                85                  90                  95
```

Thr Gly Glu Ala Phe Ala Ala Gly Leu Ala Pro Asp Cys Ala Ile Thr
            100                 105                 110

Val His His Gln Ala Asp Thr Ser Ser Pro Asp Pro Leu Phe Asn Pro
        115                 120                 125

Leu Lys Thr Gly Val Cys Gln Leu Asp Val Ala Asn Val Thr Arg Ala
    130                 135                 140

Ile Leu Arg Arg Ala Gly Gly Ser Ile Ala Asp Phe Thr Arg His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

Gln Ala Leu Pro Ser Glu Leu Lys Val Ser Ala Asp Asp Val Ser Leu
        195                 200                 205

Thr Gly Ala Val Ser Leu Ala Ser Met Leu Thr Glu Ile Phe Leu Leu
    210                 215                 220

Gln Gln Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Gln Lys Gln
        275                 280                 285

Ala Tyr Gly Val Thr Leu Pro Thr Ser Val Leu Phe Ile Ala Gly His
    290                 295                 300

Asp Thr Asn Leu Ala Asn Leu Gly Gly Ala Leu Glu Leu Asn Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
        355                 360                 365

Leu Asn Thr Pro Pro Gly Glu Val Lys Leu Thr Leu Ala Gly Cys Glu
    370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410

<210> SEQ ID NO 7
<211> LENGTH: 1230
<212> TYPE: DNA
<213> ORGANISM: Artificial Sequence
<220> FEATURE:
<223> OTHER INFORMATION: Synthetically generated polynucleotide

<400> SEQUENCE: 7
cagagtgagc cggagctgaa gctggaaagt gtggtgattg tcagtcgtca tggtgtgcgt     60
gctccaacca aggccatgca actgatgcag gatgtcaccc agacgcatg gccaacctgg    120 ccggtaaaac tgggtgagct gacaccgcgc ggtggtgagc taatcgccca tctcggacat    180
tactggcgtc agcgtctggt agccgacgga ttgctgccta atgtggctg cccgcagtct    240

-continued

| | |
|---|---|
| ggtcaggtcg cgattattgc tgatgtcgac gagcgtaccc gtaaaacagg cgaagccttc | 300 |
| gccgccgggc tggcacctga ctgtgcaata accgtacata cccaggcaga tacgtccagt | 360 |
| cccgatccgt tatttaatcc tctaaaaact ggcgtttgcc aactggatgt ggcgaacgtg | 420 |
| agacgtgcga tcctcgagag ggcaggaggg tcaattgctg actttaccgg gcattatcaa | 480 |
| acggcgtttc gcgaactgga acgggtgctt aattttccgc aatcaaactt gtgccttaaa | 540 |
| cgtgagaaac aggacgaaag ctgttcatta acgcaggcat taccatcgga actcaaggtg | 600 |
| agcgccgact gtgtctcatt aaccggtgcg gtaagcctcg catcaatgct gacggagata | 660 |
| tttctcctgc aacatgcaca gggaatgccg gagccgggt ggggaaggat caccgattca | 720 |
| caccagtgga acaccttgct aagtttgcat aacgcggtgt ttgatttgct acaacgcacg | 780 |
| ccagaggttg cccgcagccg cgccaccccg ttattagatt tgatcaagac agcgttgacg | 840 |
| ccccatccac cgcaaaaaca ggcgtatggt gtgacattac ccacttcagt gctgtttatc | 900 |
| gccggacacg atactaatct ggcaaatctc ggcggcgcac tggagctcga atggacgctt | 960 |
| cccggtcagc cggataacta tccgccaggt ggtgaactgg tgtttgaacg ctggcgtcgg | 1020 |
| ctaagcgata acagccagtg gattcaggtt tcgctggtct tccagacttt acagcagatg | 1080 |
| cgtgataaaa cgccgctgtc attaaatacg ccgcccggag aggtgaaact gaccctggca | 1140 |
| ggatgtgaag agcgaaatgc gcagggcatg tgttcgttgg caggttttac gcaaatcgtg | 1200 |
| aatgaagcac gcataccggc gtgcagtttg | 1230 |

<210> SEQ ID NO 8
<211> LENGTH: 411
<212> TYPE: PRT
<213> ORGANISM: Artificial Sequence
<220> FEATURE:
<223> OTHER INFORMATION: Synthetically generated polypeptide

<400> SEQUENCE: 8

Met Gln Ser Glu Pro Glu Leu Lys Leu Glu Ser Val Val Ile Val Ser
1               5                   10                  15

Arg His Gly Val Arg Ala Pro Thr Lys Ala Met Gln Leu Met Gln Asp
                20                  25                  30

Val Thr Pro Asp Ala Trp Pro Thr Trp Pro Val Lys Leu Gly Glu Leu
            35                  40                  45

Thr Pro Arg Gly Gly Glu Leu Ile Ala His Leu Gly His Tyr Trp Arg
        50                  55                  60

Gln Arg Leu Val Ala Asp Gly Leu Leu Pro Lys Cys Gly Cys Pro Gln
65                  70                  75                  80

Ser Gly Gln Val Ala Ile Ile Ala Asp Val Asp Glu Arg Thr Arg Lys
                85                  90                  95

Thr Gly Glu Ala Phe Ala Ala Gly Leu Ala Pro Asp Cys Ala Ile Thr
            100                 105                 110

Val His Thr Gln Ala Asp Thr Ser Ser Pro Asp Pro Leu Phe Asn Pro
        115                 120                 125

Leu Lys Thr Gly Val Cys Gln Leu Asp Val Ala Asn Val Arg Arg Ala
    130                 135                 140

Ile Leu Glu Arg Ala Gly Gly Ser Ile Ala Asp Phe Thr Gly His Tyr
145                 150                 155                 160

Gln Thr Ala Phe Arg Glu Leu Glu Arg Val Leu Asn Phe Pro Gln Ser
                165                 170                 175

Asn Leu Cys Leu Lys Arg Glu Lys Gln Asp Glu Ser Cys Ser Leu Thr
            180                 185                 190

-continued

```
Gln Ala Leu Pro Ser Glu Leu Lys Val Ser Ala Asp Cys Val Ser Leu
            195                 200                 205

Thr Gly Ala Val Ser Leu Ala Ser Met Leu Thr Glu Ile Phe Leu Leu
        210                 215                 220

Gln His Ala Gln Gly Met Pro Glu Pro Gly Trp Gly Arg Ile Thr Asp
225                 230                 235                 240

Ser His Gln Trp Asn Thr Leu Leu Ser Leu His Asn Ala Val Phe Asp
                245                 250                 255

Leu Leu Gln Arg Thr Pro Glu Val Ala Arg Ser Arg Ala Thr Pro Leu
            260                 265                 270

Leu Asp Leu Ile Lys Thr Ala Leu Thr Pro His Pro Pro Gln Lys Gln
        275                 280                 285

Ala Tyr Gly Val Thr Leu Pro Thr Ser Val Leu Phe Ile Ala Gly His
        290                 295                 300

Asp Thr Asn Leu Ala Asn Leu Gly Gly Ala Leu Glu Leu Glu Trp Thr
305                 310                 315                 320

Leu Pro Gly Gln Pro Asp Asn Tyr Pro Pro Gly Gly Glu Leu Val Phe
                325                 330                 335

Glu Arg Trp Arg Arg Leu Ser Asp Asn Ser Gln Trp Ile Gln Val Ser
            340                 345                 350

Leu Val Phe Gln Thr Leu Gln Gln Met Arg Asp Lys Thr Pro Leu Ser
            355                 360                 365

Leu Asn Thr Pro Pro Gly Glu Val Lys Leu Thr Leu Ala Gly Cys Glu
        370                 375                 380

Glu Arg Asn Ala Gln Gly Met Cys Ser Leu Ala Gly Phe Thr Gln Ile
385                 390                 395                 400

Val Asn Glu Ala Arg Ile Pro Ala Cys Ser Leu
                405                 410
```